United States Patent
Ricci et al.

(10) Patent No.: US 10,748,650 B1
(45) Date of Patent: Aug. 18, 2020

(54) MACHINE LEARNING OF DENTAL IMAGES FOR E-COMMERCE

(71) Applicants: Richard Ricci, New York, NY (US); Andrea Cambria, New York, NY (US)

(72) Inventors: Richard Ricci, New York, NY (US); Andrea Cambria, New York, NY (US)

(73) Assignees: Richard Ricci, New York, NY (US); Andrea Cambria, New York, NY (US)

( * ) Notice: Subject to any disclaimer, the term of this patent is extended or adjusted under 35 U.S.C. 154(b) by 0 days.

(21) Appl. No.: 16/683,116

(22) Filed: Nov. 13, 2019

Related U.S. Application Data

(60) Provisional application No. 62/875,319, filed on Jul. 17, 2019.

(51) Int. Cl.
| | | |
|---|---|---|
| *G16H 30/20* | (2018.01) | |
| *G16H 30/40* | (2018.01) | |
| *G06Q 30/06* | (2012.01) | |
| *A61B 6/00* | (2006.01) | |
| *G06T 7/00* | (2017.01) | |
| *G06N 3/08* | (2006.01) | |

(52) U.S. Cl.
CPC ............ *G16H 30/20* (2018.01); *A61B 6/469* (2013.01); *G06N 3/08* (2013.01); *G06Q 30/0605* (2013.01); *G06T 7/0014* (2013.01); *G16H 30/40* (2018.01); *G06T 2210/12* (2013.01); *G06T 2210/41* (2013.01)

(58) Field of Classification Search
None
See application file for complete search history.

(56) References Cited

U.S. PATENT DOCUMENTS 9,760,807 B2 * 9/2017 Zhou ...................... G06T 7/143
9,848,958 B2 * 12/2017 Matov ..................... G06F 17/11
(Continued)

OTHER PUBLICATIONS

Leonardi, Rosalia, Daniela Giordano, and Francesco Maiorana. "An evaluation of cellular neural networks for the automatic identification of cephalometric landmarks on digital images." BioMed Research International 2009 (2009). (Year: 2009).*
(Continued)

*Primary Examiner* — Michelle M Entezari

(57) ABSTRACT

Machine learning of a dental image for e-commerce is described. An aggregator server may receive dental images of an e-commerce consumer from an e-commerce provider. The dental images are matched to a probability dataset and correlated with an e-commerce consumer dataset to produce an e-commerce dataset. With different resolutions each neural network machine learns to probability map and detect different dental object probabilities. Correlated dental object probabilities of dental images, e-commerce consumer dental images, dental image datasets, e-commerce consumer datasets and e-commerce datasets are provided to e-commerce providers, e-commerce consumers, e-commerce administrators and machine learning entities which may use the data for a probability diagnosis aid, a probability demonstration aid or may buy, sell, exchange and transfer at least one of: a dental image, an e-commerce consumer dental image, a dental image dataset, an e-commerce consumer dataset, an e-commerce dataset over a communication network such as the internet.

17 Claims, 13 Drawing Sheets

(56) References Cited

U.S. PATENT DOCUMENTS

| | | | | |
|---|---|---|---|---|
| 10,019,654 B1* | 7/2018 | Pisoni | | G06K 9/3241 |
| 10,210,613 B2* | 2/2019 | Xu | | G06T 7/0012 |
| 10,268,947 B2* | 4/2019 | Wang | | G06K 9/6274 |
| 10,449,001 B2* | 10/2019 | Park | | A61F 2/3859 |
| 2011/0257998 A1* | 10/2011 | Cinqualbre | | G06Q 50/24 |
| | | | | 705/3 |
| 2016/0174902 A1* | 6/2016 | Georgescu | | G06T 7/73 |
| | | | | 600/408 |
| 2018/0168781 A1* | 6/2018 | Kopelman | | A61C 1/0015 |
| 2018/0259608 A1* | 9/2018 | Golden | | G06N 3/084 |
| 2018/0303581 A1* | 10/2018 | Martz | | A61C 9/0006 |
| 2019/0163768 A1* | 5/2019 | Gulati | | G06F 16/532 |
| 2019/0213448 A1* | 7/2019 | Peng | | G06N 3/02 |

OTHER PUBLICATIONS

Wang, Shumeng, et al. "Automatic analysis of lateral cephalograms based on multiresolution decision tree regression voting." Journal of healthcare engineering 2018 (2018). (Year: 2018).*

* cited by examiner

MACHINE LEARNING OF DENTAL IMAGES FOR E-COMMERCE

CLAIM OF PRIORITY

This application claims priority to U.S. Application 62/875,319 filed Jul. 17, 2019, the contents of which are herein fully incorporated by reference in its entirety.

FIELD OF THE EMBODIMENTS

The field of the embodiments relate to a system to provide machine learning of dental images for e-commerce. The dental image from an e-commerce consumer may be processed by a machine learning mechanism to learn the following:
(1) Machine learn to train an aggregate server to process a first, second and/or multiple dental image(s) with a deep neural network.
(2) Machine learn to match and identify dental image landmark probabilities of a dental image.
(3) Machine learn to match and identify image class landmark probabilities of a dental image.
(4) Machine learn to match and identify object class landmark probabilities of a dental image.
(5) Machine learn to match and identify spatial landmark probability relationships of a dental image.
(6) Machine learn to match and identify object probability landmarks of dental image.
(7) Machine learn to match and identify object probability relationships of a dental image.
(8) Machine learn to generate landmark probability maps of a dental image.
(9) Machine learn to match and identify landmark probability maps of a dental image.
(10) Machine learn to match and identify object class probabilities and image class probabilities of a dental image.
(11) Correlate the machined learned dental image data to a dental image dataset and merge with an e-commerce consumer dataset to produce an e-commerce dataset.
(12) Machine learn to generate a probability diagnosis and/or a probability demonstration aid from the e-commerce dataset.
(13) Machine learn to provide an e-commerce dataset to an e-commerce provider, e-commerce consumer, e-commerce administrator and/or a machine learning entity.
(14) Machine learn to process at a transaction of least one: an exchange, a transfer, a buy, a sell with at least one of: a dental image, an e-commerce consumer dental image, dental image dataset, an e-commerce consumer dataset, an e-commerce dataset over a communication network, wherein a communication network includes at least one of: the internet, an intranet, an extranet, an internet, an internet transaction service, an online transaction service, a mobile network, a wireless network, an online transaction processing (OLTP) service, an online analytical processing (OLAP) service, a transaction platform.

BACKGROUND OF THE EMBODIMENTS

Digital dental images have revolutionized the entire dental field. Today, digital radiography is common place in the vast majority of dental offices. Doctors, hygienists and staff are ubiquitously trained in the taking and computer processing of digital dental images. Digital dental images have led to huge improvements in patient diagnosis and treatment options. Digital dental x-rays are processed vastly faster than traditional film dental x-rays. In addition to this, the patient's radiation exposure is significantly less with digital dental x-rays. Patient dental image management service(s) provide a wide variety of applications ranging from offsite image hosting, dental image attachments to insurance claims, dental laboratory scans, x-ray to graphic based charting and dental charting by voice command.

SUMMARY OF THE EMBODIMENTS

The present invention and its embodiments relate to machine learning of dental images for e-commerce. A dental image may include an e-commerce consumer dental image. Wherein e-commerce is the activity of transferring at least one of: a product, goods, data, an image, information, a service over a communication network. Wherein a communication network is at least one of: the internet, an intranet, an extranet, an internet, an internet transaction service, an online transaction service, a mobile network, a wireless network, an online transaction processing (OLTP) service, an online analytical processing (OLAP), a transaction platform, an internet transaction platform. A system may provide machine learning of the dental images for e-commerce. The system may include an aggregator server. The aggregator server may be configured to receive dental images of an e-commerce consumer from an e-commerce provider. The aggregator server may be configured to process dental images of an e-commerce consumer from an e-commerce provider and/or an e-commerce administrator. An example of a dental image e-commerce provider may include a business entity, a business owner, an employer, a wholesaler, a retailer, a professional, a dentist, a dental hygienist, a dental professional, a physician, a health professional, a group, a veterinarian, a veterinarian professional, a research entity, a law enforcement entity, a public administration entity, a bioinformatics service, an insurance company and/or a cloud based storage service. An example of a dental image e-commerce consumer includes a patient, an individual, a guardian, a group and an employee. An example of an e-commerce administrator includes an administrator, an administrator entity and a governing agency. Next, the dental images for e-commerce may be processed with a machine learning computer vision image class dataset and may also be processed with a large computer vision image class dataset. A computer vision image class from the machine learned computer vision image class dataset may be matched to an individual e-commerce consumer dataset and/or larger e-commerce datasets. Both computer vision datasets and the e-commerce datasets may be merged and correlated with large datasets and provided to an e-commerce provider, an e-commerce consumer, an e-commerce administrator and/or a machine learning entity. The dental images for e-commerce may also be processed with a machine learned computer vision object class dataset. A computer vision object class from the machine learned computer vision object class dataset may be matched to an individual e-commerce consumer dataset and/or larger e-commerce datasets. Both computer vision datasets and the information dataset may be merged and correlated with large datasets and provided to e-commerce providers. In addition, a cluster analysis of the e-commerce consumer dataset may be performed with a cluster dataset to produce correlated dental images for e-commerce. Furthermore, the correlated dental images for e-commerce may be provided to a machine learning entity to compile a diagnostic probability aid for an e-commerce provider and/or an e-commerce consumer.

In another embodiment of the present invention, an aggregator server for providing machine learning of dental images for e-commerce is described. The aggregator server may include a computer vision component configured to analyze the dental images for e-commerce, a memory configured to store instructions associated with an aggregator service, and a processor coupled to the computer vision component and the memory. The processor may execute the instructions associated with the aggregator service. The aggregator service may include an image processing engine. The image processing engine may be configured to receive a dental image of an e-commerce consumer from an e-commerce provider. Another example of an e-commerce provider may include a business. Another example of an e-commerce consumer may be a consumer. Another example of an e-commerce administrator may include an administrator. E-commerce providers, e-commerce consumers and e-commerce administrators may process, exchange, transfer and share e-commerce consumer dental images and e-commerce datasets between at least one of: business to business (B2B), business to consumer (B2C), consumer to business (C2B), consumer to consumer (C2C), business to administration (B2A) and consumer to administration (C2A). Further e-commerce providers, e-commerce consumers and e-commerce administrators may use machine learning of dental images correlated with e-commerce datasets to buy and/or sell e-commerce goods and/or services over a communication network such as the internet, an intranet, an extranet, an internet, an internet transaction service, an online transaction service, a mobile network, a wireless network, an online transaction processing (OLTP) service, online analytical processing (OLAP) service, a transaction platform. The types of goods and services may be one or more of: tangible goods, physical goods (products), intangible products, digital goods, a service. The e-commerce providers, e-commerce consumers and e-commerce administrators may also buy and/or sell e-commerce consumer dental images, e-commerce consumer dental image landmark probability maps and/or e-commerce datasets. Further, the e-commerce providers, e-commerce consumers and e-commerce administrators may buy and/or sell e-commerce consumer dental image landmark probabilities, image class landmark probabilities, object class landmark probabilities, spatial landmark probability relationships, object probability landmarks, object probability relationships, and dental image landmark probability maps.

The dental images for e-commerce may next be processed with a machine learned object class dataset. An object class from the machine learned object class dataset may be matched and identified to the dental images for e-commerce. The dental images for e-commerce may be processed with a machine learned image class, an object class, a deep neural network, convolutional neural network, dental image landmark probabilities, image class landmark probabilities, object class landmark probabilities, spatial landmark probability relationships, object probability landmarks, object probability relationships, and to generate dental image landmark probability maps, image class probabilities, object class probabilities, an image confidence score, an object confidence score and e-commerce datasets.

An image class, object class and a landmark probability map of dental images may be matched and identified to the dental images of an e-commerce consumer. In addition, an e-commerce consumer dataset of an e-commerce consumer associated with the dental images for e-commerce may be queried and received from an e-commerce provider. Subsequently the dental images for e-commerce, the image class, the object class, and the landmark probability map may be inserted to an e-commerce dataset. Furthermore, a cluster analysis of an e-commerce consumer dataset's personal information may be processed with a cluster dataset to produce correlated dental images for a correlation dataset. Moreover, the correlation dataset may be provided to a machine learning entity to compile a diagnostic probability aid and/or a probability demonstration aid for an e-commerce provider and/or an e-commerce consumer.

In yet another embodiment of the present invention, a method of providing machine learning of dental images for e-commerce is described. The method may include receiving dental images of an e-commerce consumer from an e-commerce provider. An example of a dental image e-commerce provider may include a business entity, a business owner, an employer, a wholesaler, a retailer, a professional, a dentist, a dental hygienist, a dental professional, a physician, a health professional, a group, veterinarian, a veterinarian professional, a research entity, a law enforcement entity, a public administration entity, a bioinformatics service, an insurance company and/or a cloud based storage service. An example of a dental image e-commerce consumer includes a patient, an individual, a guardian, a group and an employee. An example of an e-commerce administrator includes an administrator, an administrator entity and a governing agency. An example of an e-commerce consumer dental image includes an electronically captured dental image from an e-commerce provider and/or an e-commerce consumer.

The dental images for e-commerce may next be processed with a machine learned image class dataset. An image class from the machine learned image class dataset may be matched to the dental images for e-commerce. The dental images for e-commerce may also be processed with a machine learned object class and a dental image landmark probability map dataset. An object class and a dental image landmark probability map dataset may be matched to the dental images for e-commerce. In addition, an e-commerce consumer dataset of an e-commerce consumer associated with the dental images for e-commerce may be queried and received from an e-commerce entity. Subsequently, the dental images for e-commerce, image class, object class, and dental image landmark probability maps may be inserted into the e-commerce consumer dataset. Furthermore, a cluster analysis of the e-commerce consumer dataset may be performed with a cluster dataset to produce correlated dental images for e-commerce. Moreover, the correlated dental images for e-commerce may be provided to a machine learning entity to compile a diagnostic probability aid for an e-commerce provider, an e-commerce consumer and/or an e-commerce administrator.

An e-commerce consumer, that includes at least one of: an individual, a guardian, a group, an employee, may process a transaction of at least one of: an exchange, a transfer, a buy, a sell of a dental image and/or a dataset with at least one of: an e-commerce provider, an e-commerce consumer, an e-commerce administrator, a machine learning entity in exchange for at least one of: currency, data, discounts, a product, goods, a software, an application, an advertisement. An e-commerce consumer may retain their dental images and/or their datasets on their client device that may include a server, dental office server, a network node, a desktop computer, a workstation, a laptop computer, a cell phone, a tablet, and/or a mobile device, among others. Further, if authorization is given from an e-commerce consumer, at least one of: an e-commerce provider, an e-commerce administrator, a machine learning entity may exchange, transfer, buy, sell an e-commerce consumer a dental image and/or dataset with at least one of: an e-commerce provider, an e-commerce consumer, e-commerce administrator, machine learning entity for at least one of: currency, data, discounts, a product, goods, a software, an application, advertising.

It is an object of the embodiments of the present invention to provide machine learning of a dental image for e-commerce.

It is an object of the embodiments of the present invention to machine learn to determine an image class, an object class, dental image landmark probabilities, image class landmark probabilities, object class landmark probabilities, spatial landmark probability relationships, object probability landmarks, object probability relationships, generate dental image landmark probability maps of dental image datasets of a dental image.

It is an object of the embodiments of the present invention to machine learn to correlate dental images with an e-commerce dataset(s) and perform a cluster analysis to produce correlated dataset(s).

It is an object of the embodiments of the present invention to provide the correlated dental images for e-commerce to a machine learning entity to compile a diagnostic probability aid and probability demonstration aid for an e-commerce provider, an e-commerce consumer and/or an e-commerce administrator.

It is the object of the embodiment of the present invention to correlate a dental image landmark probability map with an e-commerce dataset and provide the correlated information to e-commerce providers, e-commerce consumers, e-commerce administrators and machine leaning entities to buy and/or sell the correlated information over a communication network such as the internet, an intranet, an extranet, an internet, an internet transaction service, an online transaction service, a mobile network, a wireless network, an online transaction processing (OLTP) service, an online analytical processing (OLAP) service and/or a transaction platform.

These and other features, aspects and advantages of the present invention will become better understood with reference to the following drawings, description and claims.

DESCRIPTION OF THE PREFERRED EMBODIMENTS

Figure 1:
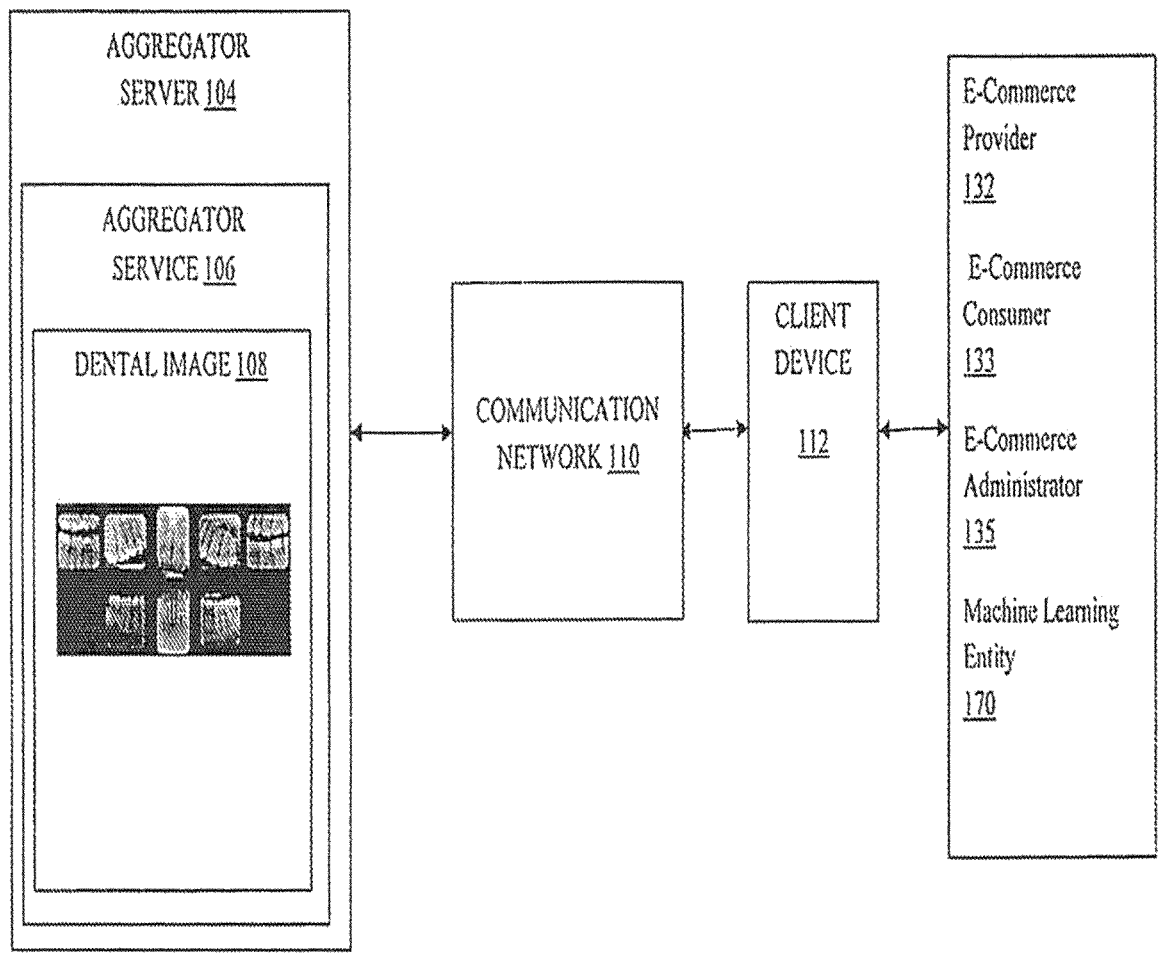
FIG. 1 shows a conceptual diagram illustrating examples of providing machine learning of dental images for e-commerce, according to an embodiment of the invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations may be made thereto.

FIG. 1 shows a conceptual diagram illustrating examples of machine learning of dental images for e-commerce. Wherein e-commerce is the activity of buying and selling of products, goods, data, images, information, and/or services over a communication network such as the internet. In an example scenario, an aggregator server 104 may execute (or provide) an aggregator service 106. The aggregator server 104 may include a physical server providing service(s), application(s), and/or an interface to client devices 112. A service (such as the aggregator service 106) may include an application performing operations in relation to a client application and/or a subscriber, among others. The aggregator server 104 may include and/or is part of a workstation, a data warehouse, a data center, and/or a cloud based distributed computing source, among others.

In an example scenario, the aggregator server 104 may execute the aggregator service 106. The aggregator service 106 may receive a dental image 108 and/or an e-commerce consumer dental image of an e-commerce consumer 133 from an e-commerce provider 132. The dental images 108 and/or an e-commerce consumer dental image of an e-commerce consumer 133 may be obtained by at least one of: a digital x-ray, a digital image, a cell phone captured image, a photographic image, a toothbrush with an imaging device, a toothbrush with an imaging device being a camera, a film based x-ray, a digitally scanned x-ray, a digitally captured x-ray, a scintillator technology based image, a trans-illumination image, a fluorescence technology based image, a blue fluorescence technology based image, a laser based technology based image, a magnetic resonance image (MRI), a cone beam computed tomography (CBCT) and a computed tomography (CT) scan based image of a section and/or an entirety of a mouth of the e-commerce consumer 133, and/or all future embodiments.

The dental image e-commerce provider 132 may utilize an image capture device and/or a storage device. The image capture device may include x-ray equipment, a digital camera, a cell phone camera, an indirect or direct flat panel detector (FPD), a charged couple device (CCD), a phosphor plate radiography device, a picture archiving and communication system (PACS), a photo-stimulable phosphor (PSP) device, a computer tomography (CT) device, a wireless complementary metal-oxide-semiconductor (CMOS), a cone beam computed tomography (CBCT) device, and/or all future embodiments.

Next, the dental images 108 of an e-commerce consumer 133 may be processed with a machine learning image class dataset. The machine learned image class dataset may include a number of dental images of an e-commerce consumer 133 from an e-commerce provider 132 with annotations associated with image class structures. An image class from the machine learned image class dataset may be matched to the dental images 108 of an e-commerce consumer 133. Furthermore, the dental images 108 of an e-commerce consumer 133 may also be processed and matched with a machine learned dental object classification dataset and a landmark probability map dataset.

Subsequently, the dental images 108, the image class, the object class, and a landmark probability map may be inserted to an e-commerce dataset associated with an e-commerce consumer 133. An e-commerce dataset may include attributes and other information associated with an e-commerce consumer. In addition, a cluster analysis of an e-commerce dataset may be performed with a cluster dataset to produce correlated dental images for a correlation dataset. The cluster dataset may include annotated information associated with a population and dental classifications associated with the population. Furthermore, the correlated dental images for e-commerce may be provided to a machine learning entity 170 to compile a diagnostic probability aid for an e-commerce provider 132, an e-commerce consumer 133 and/or an e-commerce administrator 135. An example of a dental image e-commerce consumer 133 includes a patient, an individual, a guardian, a group and an employee. The e-commerce provider 132 may include a business, a business entity, a business owner, an employer, a wholesaler, a retailer, a professional, a dentist, a dental hygienist, a dental professional, a physician, a health professional, a group, a veterinarian, a research entity, a law enforcement entity, a public administration entity, a bioinformatics service, an insurance company, and a cloud based storage service among others. An example of an e-commerce administrator includes an administrator, an administrator entity and a governing agency.

The dental images 108 of an e-commerce consumer and the e-commerce dataset and/or the correlated dental images of an e-commerce dataset may be provided to an e-commerce provider 132 through a client device 112. An example of the client device 112 may include a server, dental office server, a network node, a desktop computer, a workstation, a laptop computer, a cell phone, a tablet, and/or a mobile device, among others. The e-commerce provider 132 may be provided with an e-commerce dataset and/or the correlated dental images of an e-commerce consumer as a diagnostic probability aid. An integrated diagnostic probability aid of an e-commerce consumer 133 and/or annotated information dataset associated with the dental images for an e-commerce consumer 133 may be provided to an e-commerce provider 132, e-commerce consumer 133, e-commerce administrator 135 and/or a machine learning entity 170.

The aggregator server 104 may communicate with the client device 112 through a communication network 110. The communication network 110 may provide wired or wireless communications between network nodes such as the client device 112, and/or the aggregator server 104, among others. Previous example(s) to provide machine learning of the dental images 108 for an e-commerce consumer 133 are not provided in a limiting sense. Alternatively, the aggregator service 106 may receive the dental images from an e-commerce consumer 133, process the dental images 108, and provide the (annotated) e-commerce consumer dataset and the correlated dental images for e-commerce datasets as a desktop application, a workstation application, a cell phone application and/or a server application, among others. Client application(s) executed by the client device 112 may also include client interface(s) of (or interacting with) the aggregator service 106.

The e-commerce provider 132 may also interact with the client application(s) on the client device 112 with a keyboard based input, a mouse based input, a voice based input, a pen based input, and a gesture based input, among others. The gesture based input may include one or more touch based actions such as a touch action, a swipe action, and a combination of each, among others.

While the example system in FIG. 1 has been described with specific components including the aggregator server 104, the aggregator service 106, embodiments are not limited to these components or system configurations and can be implemented with other system configuration employing fewer or additional components.

Figure 2:
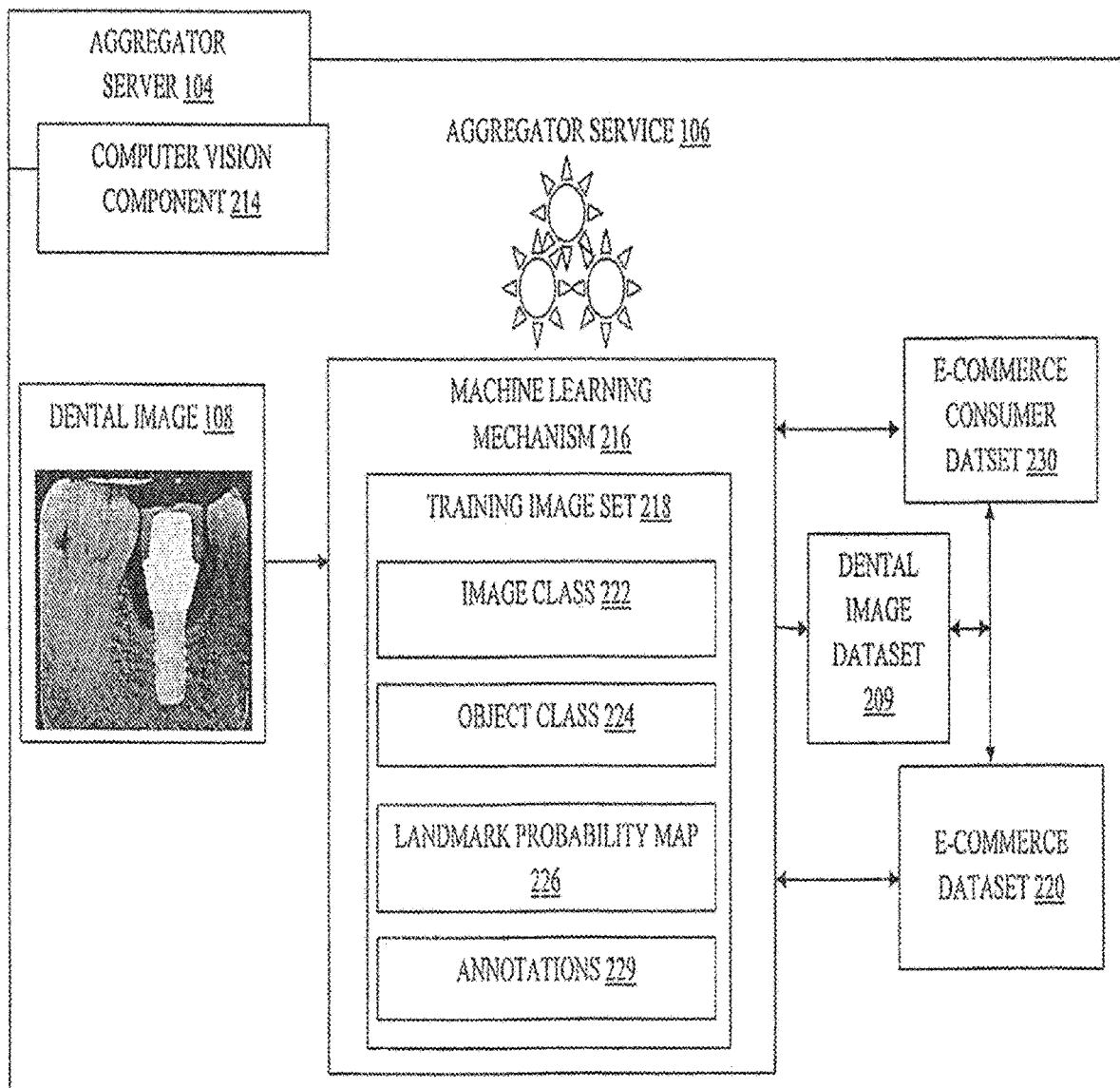
FIG. 2 shows a display diagram illustrating a machine learning mechanism to provide machine learning of dental images for e-commerce, according to an embodiment of the invention.

FIG. 2 shows a display diagram illustrating a machine learning mechanism 216 to provide machine learning of dental images for e-commerce. The aggregator server 104 may use a computer vision component 214 to execute the aggregator service 106 and process the dental images 108 for e-commerce with machine learned mechanism 216. The machine learning mechanism 216 may process the dental image 108 with an image class 222, object class 224, landmark probability map 226 and/or annotations 229. The machine learning mechanism 216 may compensate for missing information, identify and correct a discrepancy between the dental images 108 with missing information. Further, the machine learning mechanism 216 may process these images with a training image set 218 and compile into an e-commerce consumer dataset 230, a dental image dataset 209 and an e-commerce dataset 220. The machine learning mechanism may identify and correct discrepancies between the correlated e-commerce datasets 220.

Figure 3:
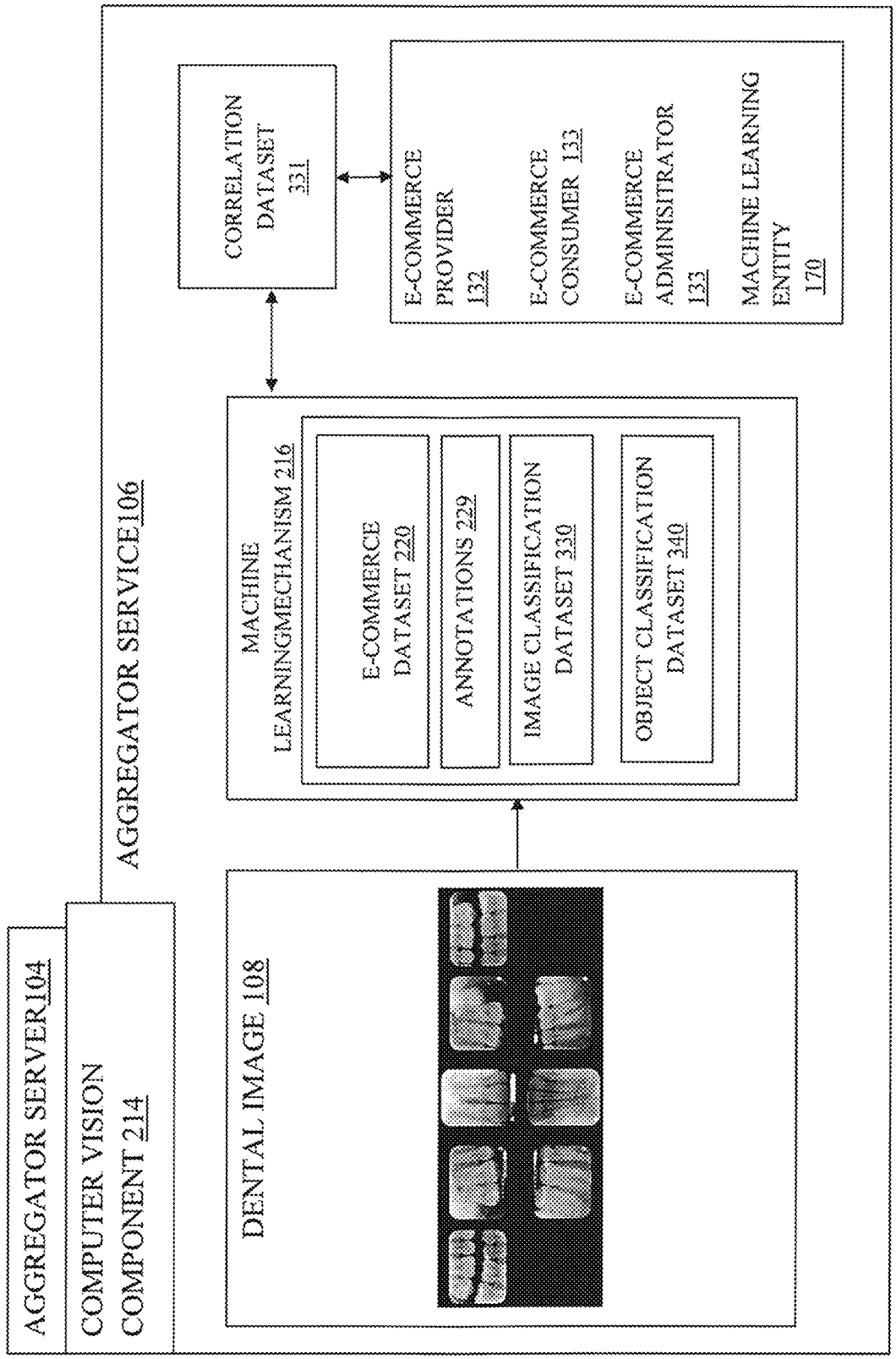
FIG. 3 shows a display diagram illustrating the processing of dental images with e-commerce datasets, annotations, image and object classification datasets to a correlation data set, according to an embodiment of the invention.

FIG. 3 shows a display diagram illustrating a machine learning mechanism 216 to provide a correlation dataset 331 from dental images 108 for e-commerce. The aggregator server 104 may process the dental images 108 with the aggregator service 106. The aggregator service 106 may process the dental images with annotations 229, e-commerce datasets 220, image classifications dataset 330 and object classifications dataset 340 to produce a correlation dataset 331. The correlation dataset 331 may be provided to an e-commerce provider 132, an e-commerce consumer 133, an e-commerce administrator 135, and/or machine learning entity 170.

Figure 4:
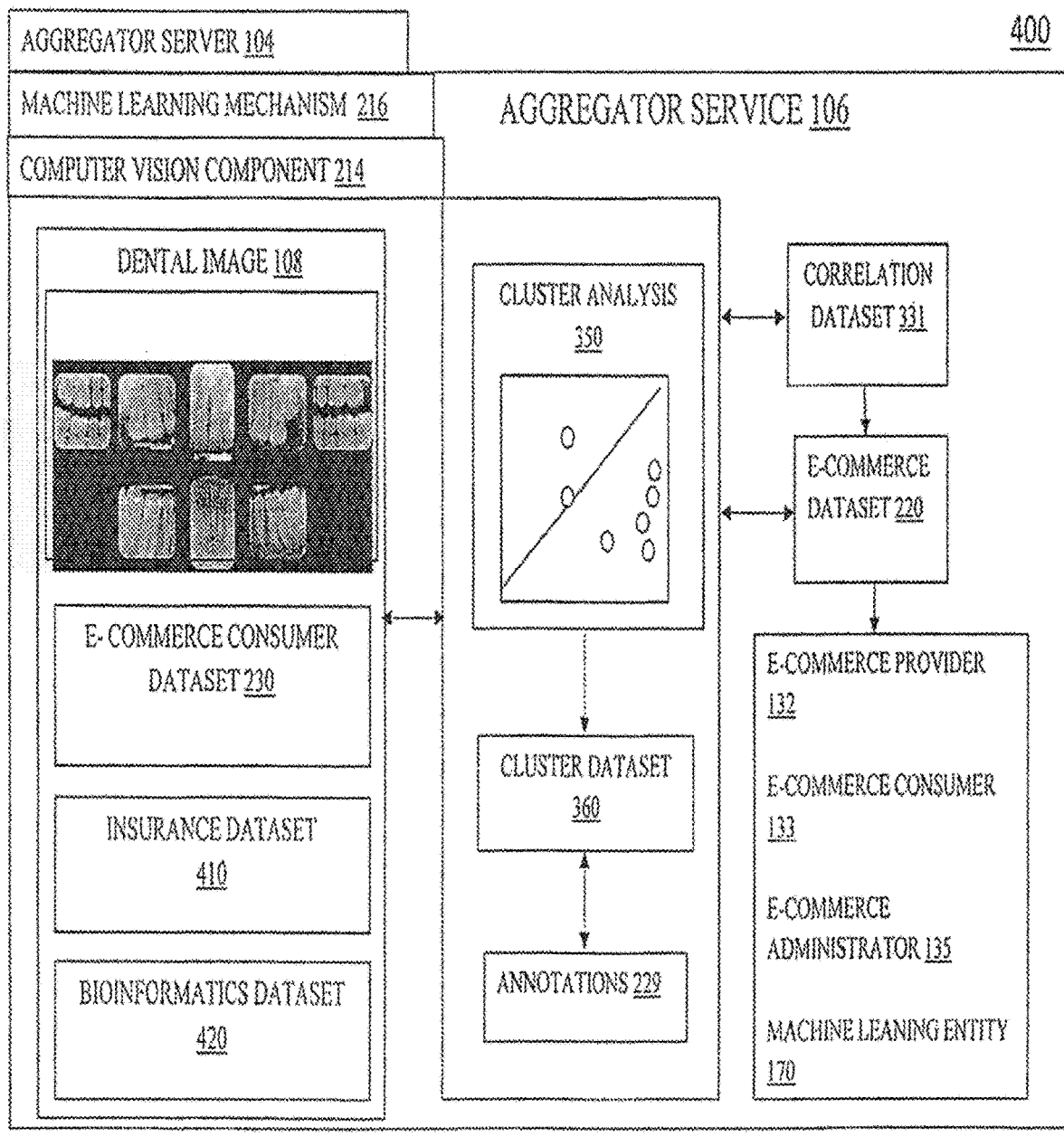
FIG. 4 shows a display diagram illustrating a cluster analysis of dental images and annotations to produce a correlation dataset for an e-commerce provider, an e-commerce consumer, an e-commerce administrator and/or a machine learning entity according to an embodiment of the invention.

FIG. 4 shows a display diagram of process 400 performing a cluster analysis 350 to produce a correlation dataset 331. The aggregator server may use a computer vision component 214 and a machine learning mechanism 216 to process dental image 108. The aggregator service 106 (executed by the aggregator server 104) may query and receive a dental image 108, an e-commerce consumer dataset 230, an insurance dataset 410 and/or a bioinformatics dataset 420. The e-commerce consumer dataset 230 may include an e-commerce consumer's personal information such as an age, a first name, a gender, a middle initial, a last name, a date of birth, a zip code, an address, a cell phone number, a land line number, a current medication, a previous medication, a social security number, a marital status, an insurance, an e-commerce consumer's insurance identification number, a change of insurance, a change of employment, a change of zip code, a change of the previous medication, a change of the marital status, a change of the gender, among others associated with the e-commerce consumer 133.

The dental images 108 from an e-commerce consumer 133, capture information associated with the dental images 108 for an e-commerce consumer 133 (such as a time, a location, and/or a source, among others), image class 222 and object class 224, may be inserted to the e-commerce dataset 220. The aggregator service 106 may also identify whether the e-commerce consumer 133 is informed in regards to a notification obligation such as a health insurance portability and accountability act (HIPAA), an end user licensing agreement (EULA), a system and method licensing agreement (SLA), a security token, a swipe authorization, and/or signed consent form by analyzing the e-commerce dataset 220 for attributes associated with the notification obligation.

Furthermore, the aggregator service 106 may compare difference(s) between the dental images 108 of an e-commerce consumer 133 (and associated annotations 229) and the attributes of the e-commerce dataset 220. The dental images 108 may be associated with annotations 229 and processed with a cluster analysis 350. The cluster analysis may be merged into a cluster dataset 360 to be compiled into a correlation dataset 331. The aggregator service 106 may recognize, label, and/or classify the correlation dataset 331 of an e-commerce consumer 133 (and the associated annotations 229) based on the e-commerce dataset 220 (and/or attributes) with a machine learning mechanism 216. The correlation datasets 331 may be provided to an, e-commerce provider 132, an e-commerce consumer 133, an e-commerce administrator 135, and/or a machine learning entity 170.

A cluster analysis 350 of the dental images 108 of an e-commerce consumer dataset 230 and/or the e-commerce dataset 220 may be performed with a cluster dataset 360 to produce correlated dental images for an e-commerce provider 132. The cluster dataset 360 may include annotated information associated with a population and dental classifications associated with the population. The cluster analysis 350 may compare attributes of the e-commerce dataset 220 (such as the capture information, the object class 224, the image class 222, and/or the landmark probability map 226) to elements of the cluster dataset 360. As such, the correlated dental images for an e-commerce provider 132 may include attributes of the e-commerce consumer dataset 230.

Furthermore, the cluster analysis 350 may be performed based on a spatial detection, a sequential pattern mining, dataset(s) comparison, a data analysis, a statistical data analysis, a Boolean Logic analysis, a fuzzy logic analysis, a machine learned analysis and/or an anomaly detection analysis mechanism, among others. In addition, the correlated dental images for an e-commerce provider 132 may be merged into the cluster dataset 360 to produce a future cluster analysis with an expanded version of the cluster dataset 360.

In addition, the aggregator service 106 may compare difference(s) between the dental images from an e-commerce provider 132 (and associated annotations 229) and the elements of the cluster dataset 360. The aggregator service 106 may recognize, label and/or classify the dental images from an e-commerce provider 132 (and the associated annotations 229) based on the element(s) the cluster dataset 360 and/or attributes.

FIG. 4 can be used as an example of a transmission of dental images 108 from an e-commerce consumer 133 to an e-commerce provider 132 and/or a machine learning service, wherein an e-commerce provider and/or a machine learning service includes a dental insurance service. A dental insurance service may include an insurance company and/or a claims data warehouse. In an example scenario, the machine learning entity 170 may include an insurance machine learning service. A dental insurance service may be an insurance company. The insurance machine learning service may be provided by a dental insurance and/or a medical insurance organization. The aggregator service 106 may correlate a dental image 108 and an e-commerce consumer dataset 230 and analyze with an insurance dataset 410. As such, the correlated dental images of an e-commerce consumer 133 may include attributes of the e-commerce dataset 220 (such as the dental images 108 for e-commerce and the annotations 229) that are further annotated with elements of the insurance dataset. The aggregator service 106 may also format the correlated dental images for an e-commerce provider 132 with an insurance claim. In addition, the aggregator service 106 may integrate the correlated dental images for an e-commerce consumer 133 to a new or an existing insurance claim. The correlation dataset 331 and an e-commerce dataset 220 may also be analyzed and merged (or integrated) into the insurance dataset 410 to expand the insurance dataset 410 for a future analysis.

The aggregator service 106 may also identify whether the e-commerce consumer 133 is informed in regards to a notification obligation such as a HIPAA, an EULA, a SLA, a security token, a swipe authorization, and/or signed consent form by analyzing the correlated dental images for e-commerce dataset 220 (annotated with the insurance dataset 410) for attributes associated with the notification obligation. The aggregator server 106 may use quantum encryption of an dental image 108 and an e-commerce dataset 220. The aggregator server 106 may also use quantum encryption of an e-commerce provider's dental image dataset and e-commerce provider's information dataset.

The aggregator service 106 may also identify discrepancy(s) between dental insurance claim(s) by analyzing and comparing attributes of the correlated dental images of an e-commerce consumer 133 and an e-commerce dataset 220 with elements of the insurance dataset 410 including American Dental Association (ADA) code(s), a date, a claim identifier, a claim number, multiple or duplicate claims (instead of a single claim), a national provider identification number for provider/institution(s) and/or a provider's state license number, among others. Corrective action to merge the discrepancy(s) may be implemented automatically to remove the discrepancy(s) between the correlated dental images for an e-commerce consumer 133, the e-commerce dataset 220, and/or the insurance claim(s) from the insurance dataset. Alternatively, corrective action may be implemented manually based on feedback and/or input from an e-commerce provider 132, e-commerce consumer 133 and/or an e-commerce administrator 135 associated with the aggregator service 106 regarding the discrepancy(s).

In another example scenario, a machine learning entity 170 may include a bioinformatics machine learning service. A bioinformatics service may be a genetic testing service and/or a geneotyping service. The bioinformatics machine learning service may be provided by a bioinformatics organization (such as a personal genomic or research organization). The aggregator service 106 may correlate dental image 108, the e-commerce dataset 220 and the correlation dataset 331 (which includes annotations 229) with a bioinformatics dataset 420. As such, the correlated dental images for an e-commerce consumer 133 may include attributes of an e-commerce dataset 220 (such as the dental images 108 for e-commerce and the annotations 229) that are further annotated with elements of the bioinformatics dataset 420. The correlated dental images for e-commerce dataset 220 may also be merged into the bioinformatics dataset 420 to expand the bioinformatics dataset 420 for a future analysis.

The aggregator service 106 may also identify whether an e-commerce consumer 133 is informed in regards to a notification obligation such as a HIPAA, an EULA, a SLA, a security token, a swipe authorization, and/or signed consent form by analyzing the e-commerce dataset 220 for attributes associated with the notification obligation.

The aggregator service 106 may also identify matching elements of the bioinformatics dataset 420 including gene(s), a gene identifier, a gene sequence, single nucleotide polymorphism(s), nucleic acid sequence(s), protein sequence(s) (proteomics), annotating genome(s), a shotgun sequence, an associated periodontal disease, a caries susceptibility, an impacted tooth, a tooth loss, an angle's classification of malocclusion, level(s) of immunoglobulin G (IGG) and immunoglobulin A (IGA), and/or diabetes diagnosis, among others by matching the attributes of the correlated dental images of the e-commerce dataset 220 with elements of the bioinformatics dataset 420. The attributes of the correlated dental images for e-commerce dataset 220 may further be annotated with the elements matched from the bioinformatics dataset 420.

In another example scenario, the aggregator service 106 may verify an authorization by an e-commerce consumer 133 to allow an analysis of dental images and the e-commerce dataset 220. In response to a determination that the e-commerce consumer authorized the analysis of the dental images and information dataset for e-commerce, the aggregator service 106 may continue with processing the dental images for e-commerce with the machine learned image class dataset and machine learned object class dataset. In response to a failure to verify the authorization by the e-commerce consumer 133, the aggregator service 106 may stop operations associated with the dental images for e-commerce.

In yet another example scenario, the aggregator service 106 may verify compliance of the dental images 108 for e-commerce and/or the correlated e-commerce dataset 220 with a regulatory policy. The aggregate service 106 may also use quantum encryption to verify compliance of the dental images for e-commerce and/or correlate an e-commerce consumer dataset 220. An example of the regulatory policy may include a HIPAA regulation. In response to a determination that the dental images for e-commerce and/or the correlated e-commerce dataset 220 may be compliant with the regulatory policy, the aggregator service 106 may provide the correlated dental images for an e-commerce consumer 133 and/or the e-commerce dataset 220 to the machine learning entity 170 for further processing and to compile a diagnostic probability aid for an e-commerce provider 132 and or an e-commerce consumer 133. Alternatively, if the dental images for e-commerce and/or the correlated dental images of the e-commerce dataset 220 may be determined as not in a compliance of the regulatory policy then the dental images for an e-commerce consumer 133 and/or the e-commerce dataset 220 may not be provided to an e-commerce provider 132, an e-commerce consumer 133, an e-commerce administrator 135 and/or a machine learning entity 170 for further processing.

Figure 5:
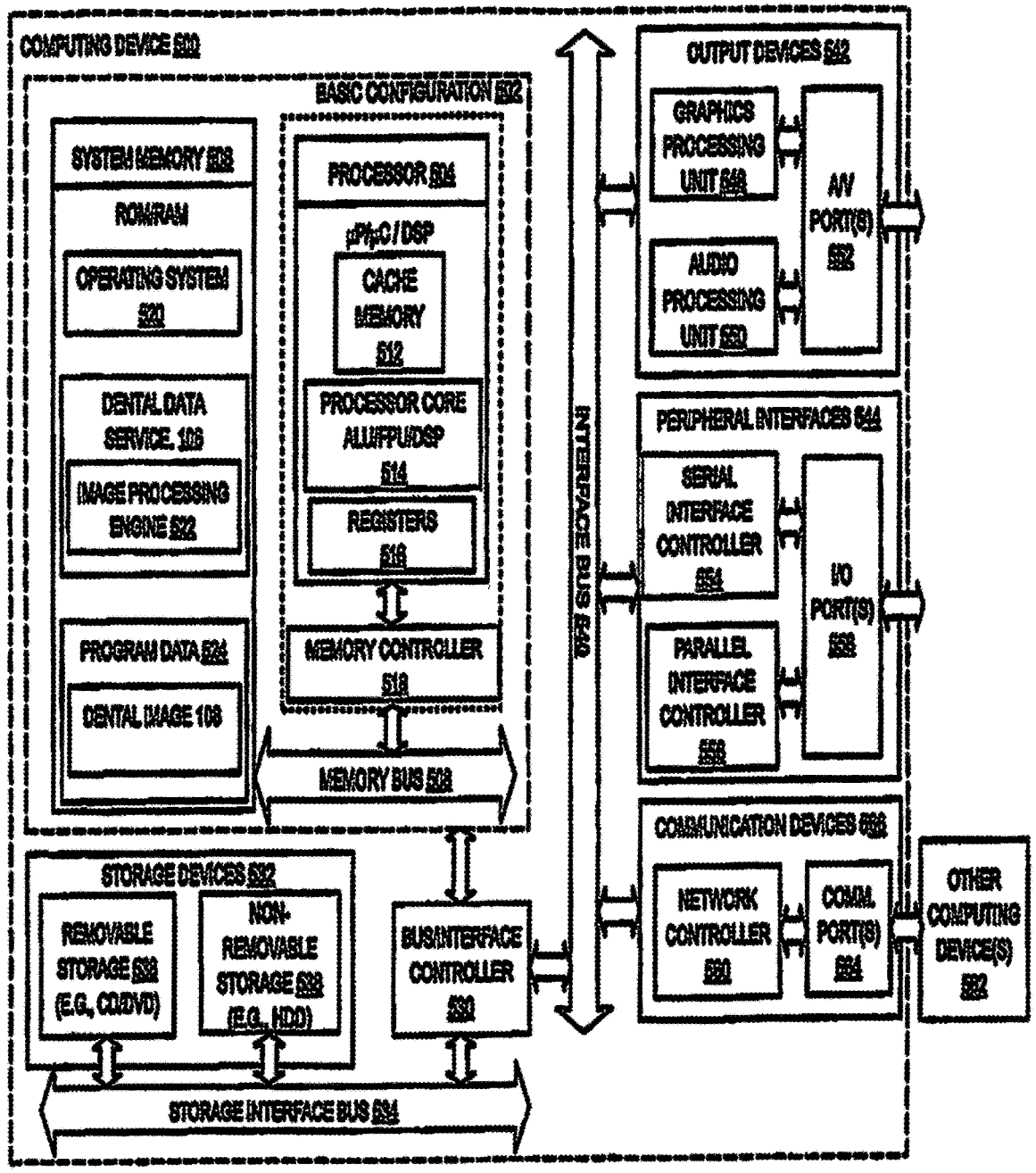
FIG. 5 is a block diagram of an example computing device, which may be used to provide machine learning of dental images for e-commerce, according to an embodiment of the invention.

FIG. 5 is a block diagram of an example computing device, which may be used to provide machine learning of dental images for e-commerce, according to embodiments.

For example, computing device 500 may be used as a server, desktop computer, portable computer, smart phone, cell phone, special purpose computer, or similar device. In a basic configuration 502, the computing device 500 may include one or more processors 504 and a system memory 506. A memory bus 508 may be used for communication between the processor 504 and the system memory 506. The basic configuration 502 may be illustrated in FIG. 5 by those components within the inner dashed line.

Depending on the desired configuration, the processor 504 may be of any type, including but not limited to a microprocessor (μP), a microcontroller (μC), a digital signal processor (DSP), or any combination thereof. The processor 504 may include one more levels of caching, such as a level cache memory 512, one or more processor cores 514, and registers 516. The example processor cores 514 may (each) include an arithmetic logic unit (ALU), a floating-point unit (FPU), a digital signal processing core (DSP Core), a graphics processing unit (GPU), or any combination thereof. An example memory controller 518 may also be used with the processor 504, or in some implementations, the memory controller 518 may be an internal part of the processor 504.

Depending on the desired configuration, the system memory 506 may be of any type including but not limited to volatile memory (such as RAM), non-volatile memory (such as ROM, flash memory, etc.), or any combination thereof. The system memory 506 may store and provide an operating system 520, an aggregator service 106, and a program data 524. The aggregator service 106 may include components such as an image processing engine 522. The image processing engine 522 may execute the instructions and processes associated with the aggregator service 106. In an example scenario, the image processing engine 522 may receive a dental image of an e-commerce consumer 133 from an e-commerce provider 132. Next, the dental images 108 for e-commerce may be processed with a machine learning mechanism 216. An image class 222 may be matched to an e-commerce dataset 220 for e-commerce providers. The dental images for e-commerce may also be processed with a machine learned object class 224 and landmark probability map 226. An image class 222, an object class 224, a landmark probability map 226 and annotations 229 may be matched to the dental images for an e-commerce consumer 133. Subsequently, the dental images for e-commerce, an image class 222, an object class 224, dental image landmark probability map 226, dental image landmark probabilities, image class landmark probabilities, object class landmark probabilities, spatial landmark probability relationships, object probability landmarks, object probability relationships, landmark probability maps, probability diagnosis and/or a probability demonstration aid may be inserted to an e-commerce dataset 220 associated with the e-commerce consumer 133. In addition, a cluster analysis 350 of the dental images 108, cluster dataset 360, annotations 229 and the e-commerce dataset 220 may be processed to produce a correlation dataset 331. Furthermore, the correlation dataset 331 may be provided to an e-commerce provider 132, an e-commerce consumer 133, an e-commerce administrator 135 and/or a machine learning entity 170 to compile a diagnostic probability aid.

Input to and output out of the aggregator service 106 may be transmitted through a communication device 566 that may be communicatively coupled to the computing device 500. The communication device 566 may provide wired and/or wireless communication. The program data 524 may also include, among other data, the dental images for e-commerce 108, or the like, as described herein. The dental images 108 for e-commerce may include an x-ray image and/or a digital image of dental structure(s) of an e-commerce consumer 133.

The computing device 500 may have additional features or functionality, and additional interfaces to facilitate communications between the basic configuration 502 and any desired devices and interfaces. For example, a bus/interface controller 530 may be used to facilitate communications between the basic configuration 502 and one or more data storage devices 532 via a storage interface bus 534. The data storage devices 532 may be one or more removable storage devices 536, one or more non-removable storage devices 538, or a combination thereof. Examples of the removable storage and the non-removable storage devices may include magnetic disk devices, such as flexible disk drives and hard-disk drives (HDDs), optical disk drives such as compact disk (CD) drives or digital versatile disk (DVD) drives, solid state drives (SSDs), tape drives, flash memory, cloud based storage, a cloud computing platform providing a storage service, an open or a closed source platform providing a storage service, a virtual private network (VPN) providing a storage service, an ISO image disk, a cloud based storage service, a redundant array of independent disks (RAID), a USB based disk drive, a USB flash drive, a storage virtualization based storage service, a digital video service, a virtualized server providing a storage service, a super computer providing a storage service, a super computer parallel array providing a storage service, a dental practice management software providing a storage service, a dental digital x-ray software providing a storage service, and/or all future embodiments. Example computer storage media may include volatile and nonvolatile, removable, and non-removable media implemented in any method or technology for storage of information, such as computer-readable instructions, data structures, program modules, all future embodiments, or other data.

The system memory 506, the removable storage devices 536 and the non-removable storage devices 538 are examples of computer storage media. Computer storage media includes, but is not limited to, RAM, ROM, EEPROM, flash memory or other memory technology, CD-ROM, digital versatile disks (DVDs), solid state drives, or other optical storage, quantum memory, magnetic cassettes, magnetic tape, magnetic disk storage or other magnetic storage devices, or any other medium which may be used to store the desired information and which may be accessed by the computing device 500. Any such computer storage media may be part of the computing device 500.

The computing device 500 may also include an interface bus 540 for facilitating communication from various interface devices (for example, one or more output devices 542, one or more peripheral interfaces 544, and one or more communication devices 566) to the basic configuration 502 via the bus/interface controller 530. Some of the example output devices 542 include a graphics processing unit 548 and an audio processing unit 550, which may be configured to communicate to various external devices such as a display or speakers via one or more A/V ports 552. One or more example peripheral interfaces 544 may include a serial interface controller 554 or a parallel interface controller 556, which may be configured to communicate with external devices such as input devices (for example, keyboard, mouse, pen, voice input device, touch input device, etc.) or other peripheral devices (for example, printer, scanner, etc.) via one or more I/O ports 558. An example of the communication device(s) 566 includes a network controller 560, which may be arranged to facilitate communications with one or more other computing devices 562 over a network communication link via one or more communication ports 564. The one or more other computing devices 562 may include servers, computing devices, and comparable devices.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

The computing device 500 may be implemented as a part of a specialized server, mainframe, or similar computer, which includes any of the above functions. The computing device 500 may also be implemented as a personal computer including both laptop computer and non-laptop computer configurations. Additionally, the computing device 500 may include specialized hardware such as an application-specific integrated circuit (ASIC), a field programmable gate array (FPGA), a programmable logic device (PLD), and/or a free form logic on an integrated circuit (IC), among others.

Example embodiments may also include methods to provide machine learning of dental images for e-commerce. These methods can be implemented in any number of ways, including the structures described herein. One such way may be by machine operations, of devices of the type described in the present disclosure. Another optional way may be for one or more of the individual operations of the methods to be performed in conjunction with one or more human operators performing some of the operations while other operations may be performed by machines. These human operators need not be collocated with each other, but each can be only with a machine that performs a portion of the program. In other embodiments, the human interaction can be automated such as by pre-selected criteria that may be machine automated.

Figure 6:
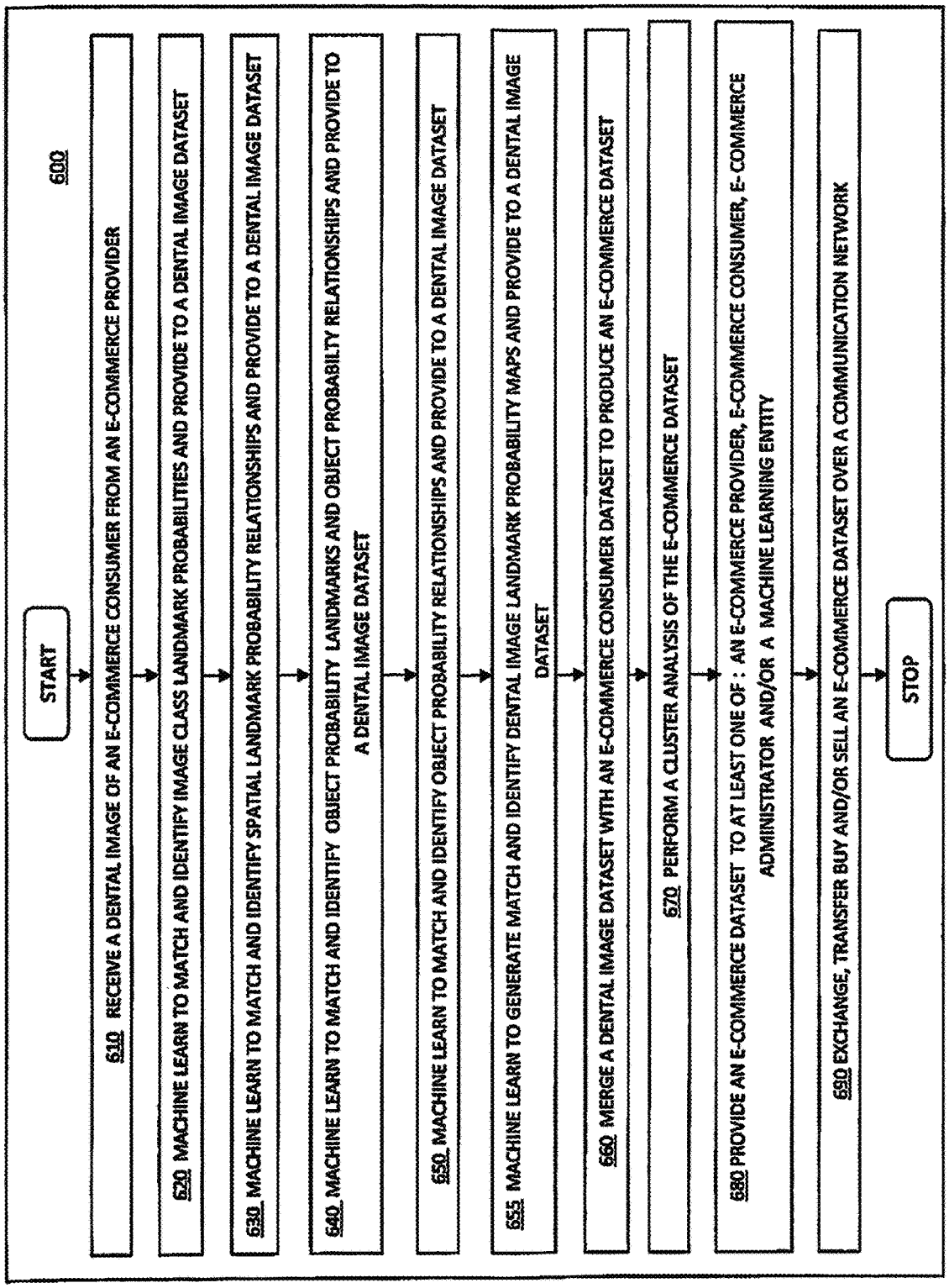
FIG. 6 is a logic flow diagram illustrating a process for providing machine learning of dental images for e-commerce, according to an embodiment of the invention.

FIG. 6 is a logic flow diagram. Process 600 begins with operation 610, where an aggregator service may receive a dental image of an e-commerce consumer 133 from an e-commerce provider 132. Next, at operation 620, the dental image from an e-commerce provider 132 may processed to machine learn to match and identify image class landmark probabilities and provide to a dental image dataset. At operation 630, the dental image for e-commerce may be processed to machine learn to match and identify spatial landmark probability relationships and provide to a dental image dataset. At operation 640, the dental image for e-commerce may also be processed to machine learn to match and identify object probability landmarks and object probability relationships and provide to a dental image dataset. Operation 650 may use machine learning to match and identify object probability relationships and provide to a dental image dataset. At operation 655 machine learning to generate, match and identify dental image landmark probability maps and provide to a dental image dataset may be utilized. Subsequently, at operation 660, the aggregate server may merge a dental image dataset with an e-commerce consumer dataset to produce an e-commerce dataset.

In addition, at operation 670, perform a cluster analysis of the e-commerce dataset, a dental image dataset 209 and an e-commerce dataset 220 may be processed with a cluster analysis 350 to produce a correlated large dataset for e-commerce providers 132, e commerce consumers 133, e-commerce administrators 135 and/or a machine learning entity 170. At operation 680, the correlated dental images and e-commerce dataset 220 may be provide to an e-commerce dataset to at least one of: an e-commerce provider, an e-commerce consumer, an e-commerce administrator, a machine learning entity. Further, at operation 690, process at least one of: an exchange, a transfer, a buy, a sell of an e-commerce dataset over a communication network.

The operations included in process 600 are for illustration purposes. Machine learning of dental images for e-commerce may be implemented by similar processes with fewer or additional steps, as well as in different order of operations using the principles described herein. The operations described herein may be executed by one or more processors operated on one or more computing devices, one or more processor cores, specialized processing devices, and/or special purpose processors, among other examples.

A method of providing machine learning of dental images for e-commerce is also described. The method may include receiving dental images 108 for e-commerce of an e-commerce consumer 133 from an e-commerce provider 132. The dental images for e-commerce may next be processed with a machine learned image class dataset. An image class from the machine learned image class dataset may be matched to the dental images for e-commerce. The dental images for e-commerce may also be processed with a machine learned object class and an e-commerce dataset 220. An object class and an e-commerce consumer dataset 230 may be matched to the dental images for an e-commerce provider 132. In addition, an e-commerce consumer dataset 230 of an e-commerce consumer 133 associated with the dental images 108 for e-commerce may be queried and received from an e-commerce provider 132. Subsequently, the dental images for e-commerce, the image class, the object class, dental image landmark probabilities, image class landmark probabilities, object class landmark probabilities, spatial landmark probability relationships, object probability landmarks, object probability relationships, and dental image landmark probability maps may be correlated with an e-commerce dataset 220. Furthermore, a cluster analysis 350 of the e-commerce dataset 220 may be performed with a cluster dataset 360 to produce a correlated dental images dataset for an e-commerce provider 132. Moreover, the correlated dental images for an e-commerce dataset 220 may be provided to e-commerce provider 132, an e-commerce consumer 133, an e-commerce administrator 135 and/or a machine learning entity 170.

Figure 7:
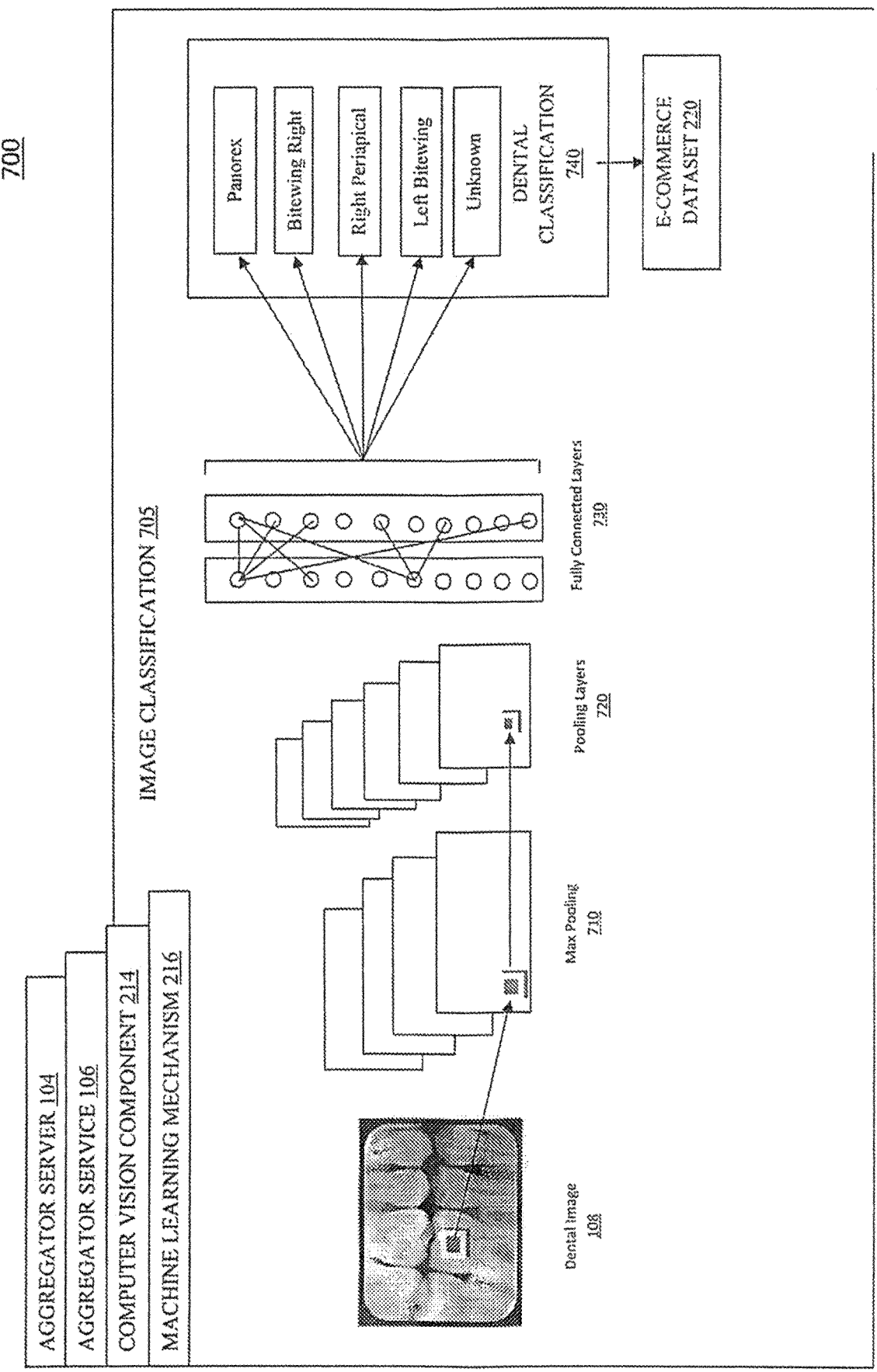
FIG. 7 shows a display diagram of a machine learning mechanism of a dental image being processed with a convolutional neural network to produce a dental classification, according to an embodiment of the invention.

FIG. 7 shows a display diagram illustrating an image classification 705 function to provide machine learning of dental images for e-commerce. The aggregator server 104 may use a computer vision component 214 to execute the aggregator service 106 and processes the dental images 108 for e-commerce with an image classification 705 function. Process 700 starts with a first resolution dental image 108 of an e-commerce consumer 133. An e-commerce dental image 108 and/or the e-commerce dataset 220 may be processed with an image classification 705 function to produce a dental classification 740. The image classification 705 may compare attributes of the e-commerce dataset 220 (the capture information, image class 222 and object class 224) to elements of the image classification dataset 330. As such, the correlated dental images for an e-commerce provider 132 may include attributes of the e-commerce dataset 220 (such as the dental images 108 for e-commerce and the annotations 229) that are further annotated with elements of the image classification dataset 330. The process may be repeated and compared to a second resolution dental image 108 and/or multiple resolution dental images 108.

Furthermore, image classification 705 may be performed based on using a convolutional neural network which may include N images and K classes to produce a training set. A training set classifier may also process dental images of an e-commerce consumer 133 with a max pooling 710 and pooling layers 720. The dental images of an e-commerce consumer 133 may then be processed with sliding window components to produce fully connected layers 730 of dental images. The fully connected layers may then be processed into dental classifications 740. Wherein, the dental classifications may include image classes 222 and object classes 224. The dental classifications may be merged with an e-commerce dataset 220. The e-commerce dataset 220 may be provided to an e-commerce provider 132, an e-commerce consumer 133, an e-commerce administrator 135 and/or an machine learning entity 170.

Figure 8:
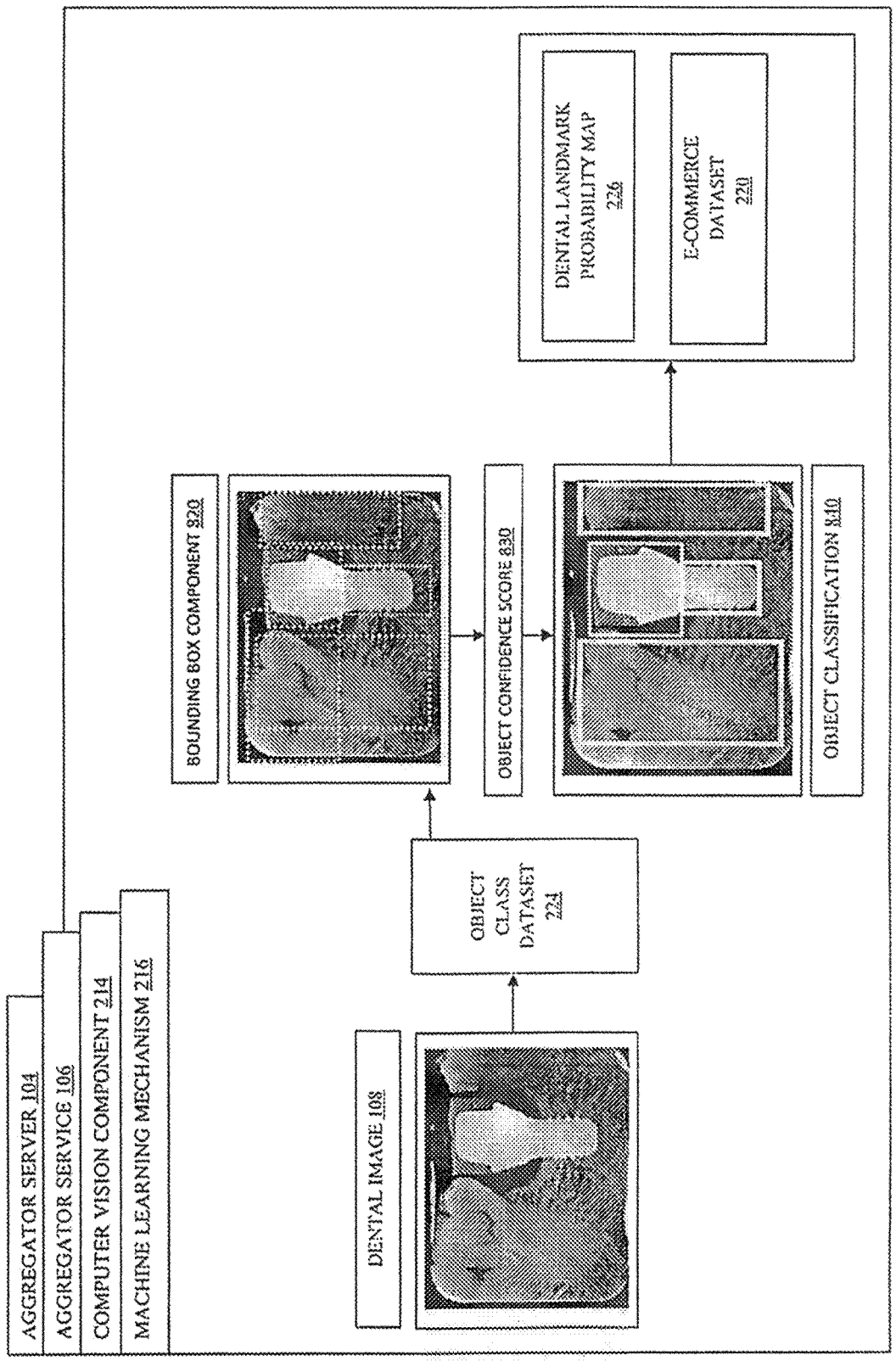
FIG. 8 shows a display diagram of a computer vision component of a dental image being processed with bounding boxes to produce a dental object class, according to an embodiment of the invention.

FIG. 8 shows a display diagram. The aggregator server 104 may use a computer vision component 214 to execute the aggregator service 106 and process the dental image 108 with a machine learning mechanism 216. Process 800 begins with a first resolution dental image 108 of an e-commerce consumer 133 that may be processed with a multiple grid component. The dental image 108 may be further processed by a object class dataset 224. The object class dataset 224 may be processed by a bounding box component 820 to generate bounding boxes around Region of Interest (ROI) of the dental image 108. Individual and/or multiple bounding boxes may be further processed into an object confidence score 830 then processed with an object classification 840. The bounding box component 820 and the object classification 840 may be merged into a dental landmark probability map 226. The process may be repeated and compared to a second resolution dental image 108 and/or multiple resolution dental images 108.

Furthermore, a dental image 108, an object class dataset (224), a bounding box component 820, an object confidence score 830, an object classification 840, dental image probability map 226 and/or an e-commerce dataset 220 may be processed with a convolutional neural network. Examples of a convolutional neural network may include Regional based Convolutional Neural Networks (R-CNN), Fast Regional based Convolutional Neural Networks (Fast R-CNN) and Faster Regional based Convolutional Neural Networks (Faster R-CNN). R-CNN may use object bounding boxes, non object bounding boxes, proposed regions, blobby images regions, a selective search, a support vector machine (SVM), a bounding box component 820, an object confidence score 830, an object classification 840, supervised training and unsupervised training to process dental images. Fast R-CNN may use a ROI pooling, bounding boxes, region proposals, a softmax layer, a bounding box component 820, an object confidence score 830, an object classification 840, supervised training and unsupervised training to process dental images. Faster R-CNN may use region proposal networks (RPN), bounding boxes, a softmax layer, anchors, a ROI pooling, ground truth boxes, a bounding box component 820, an object confidence score 830, an object classification 840, supervised learning and unsupervised learning to process dental images.

A machine learning mechanism 216 may merge and/or compare dental images to an object class dataset 224 to generate an object confidence score 830 and/or a object classification 840 to produce a dental image probability map 226. An object confidence score and/or an object classification of a dental image processed with CNN may be correlated to a dental landmark probability map 226 and further merged to an e-commerce dataset 220 and provided to an e-commerce provider 132, an e-commerce consumer 133, an e-commerce administrator 135 and/or a machine learning entity 170.

Figure 9:
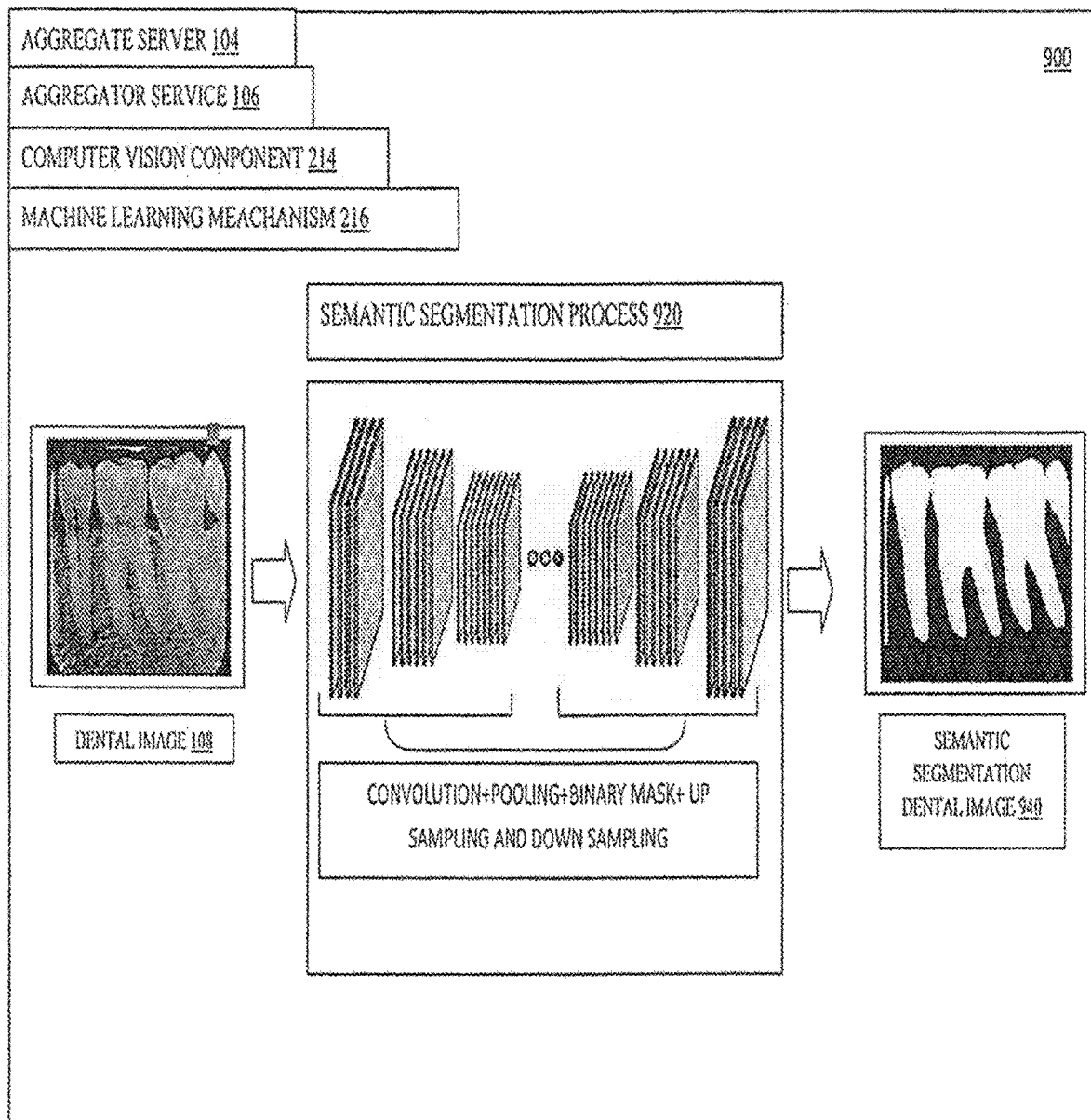
FIG. 9 shows a display diagram of a machine learning mechanism of a dental image being processed with multiple resolutions to produce dental images that show a semantic segmentation process, according to an embodiment of the invention.

FIG. 9 shows a display diagram illustrating semantic segmentation of a dental image 108. The aggregator server 104 may process an e-commerce consumer's dental image 108 with the aggregator service 106, computer vision component 214 and a machine learning mechanism 216. Process 900 is an example scenario of a dental image being processed with semantic segmentation. A dental image 108 from an e-commerce consumer 133 may be processed with a semantic segmentation process 920 to produce a semantic segmentation dental image 940 for an e-commerce provider 132. The semantic segmentation process 900 may correlate attributes of the object class dataset 224, bounding box component 820, image confidence score 830, object classification 840, dental landmark probability map 226, to elements of the semantic segmentation dental image 940. The segmentation dental image 940 may be processed with a machine learning mechanism 216. The semantic segmentation dental image 940 may be provided to an e-commerce dataset 220. The dental image 108 of semantic segmentation process 920 may also be processed with transfer learning, stem layers, Atrous spatial pyramid pooling (ASPP) and a Neural Architecture Search (NAS).

Furthermore, semantic segmentation process 920 may be performed based on a using delineation of dental image boundaries, convolution, forward inferences, backward learning, pooling, up sampling and down sampling, class identification (class ID), class identification label (class ID label) and a binary mask. An example of delineated boundaries of an dental image is the black and white junction between the tooth images and a dental image background in semantic segmentation 940. This delineated semantic segmentation example is depicted in black and white. Delineated bounded image may be processed and represented in gray scale or color scale. Delineated bounded image may be colored at the pixel level and an e-commerce consumer's dental image 108 may be processed with an Intersection over Union (IOU) feature. Dental image objects may also be processed with a first resolution, a second resolution and multiple resolutions. The processed semantic segmentation dental images may be correlated to an e-commerce dataset 220 and provided to an e-commerce provider 132, an e-commerce consumer 133, an e-commerce administrator 135 and/or a machine learning entity 170. The processed semantic segmentation dental images 940 and the e-commerce dataset 220 may be further processed with an instance segmentation process 1000.

Figure 10:
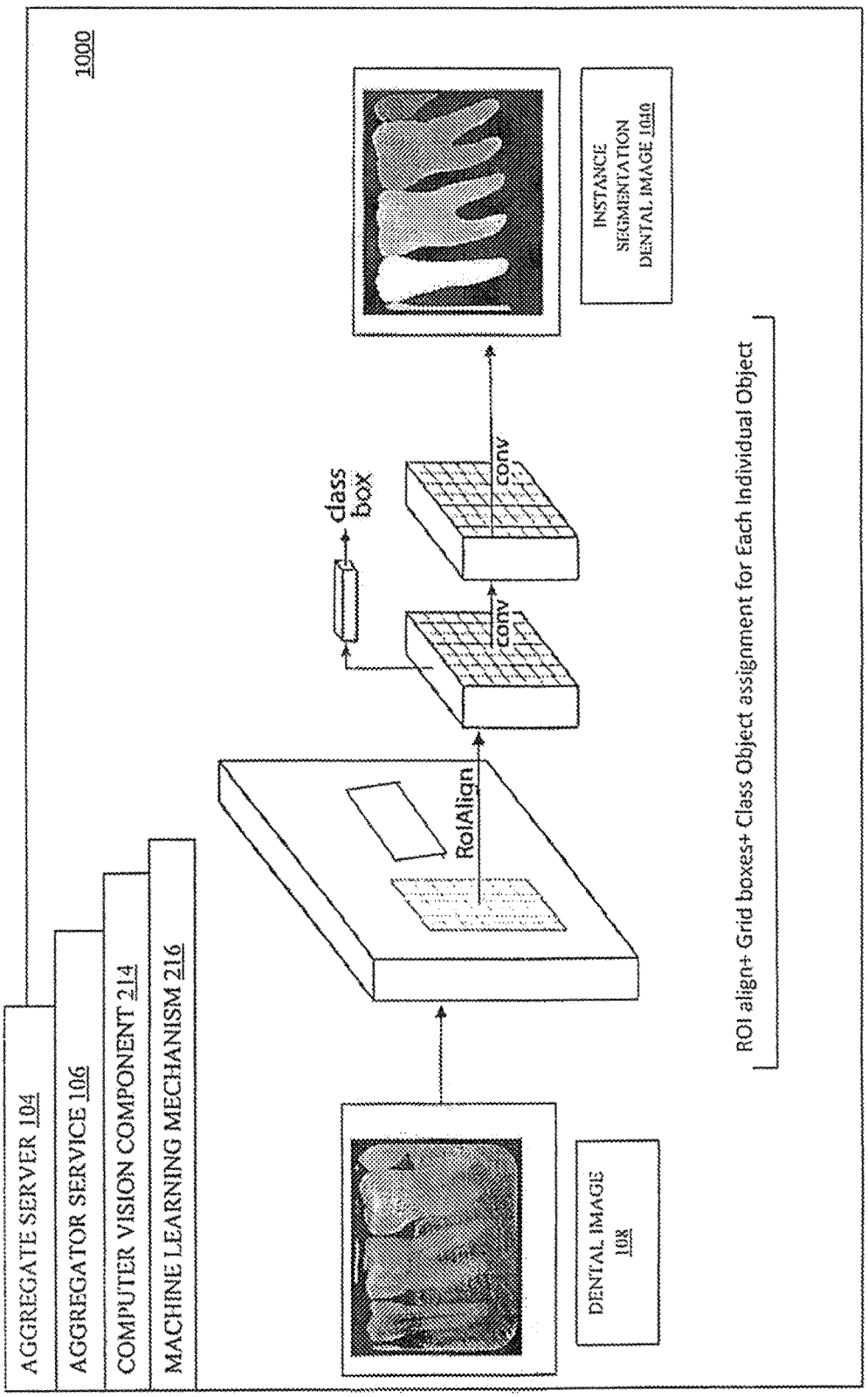
FIG. 10 shows a display diagram of a machine learning mechanism of a dental image being processed with multiple resolutions to produce dental images that shows an instance segmentation process, according to an embodiment of the invention.

FIG. 10 shows a display diagram illustrating an instance segmentation process 1000 of a dental image 108 for e-commerce. The aggregator server 104 may process e-commerce dental images 108 with the aggregator service 106, computer vision component 214 and a machine learning mechanism 216. A dental image 108 may be processed with an instance segmentation function to produce an instance segmentation dental image 1040 for an e-commerce provider 132. The instance segmentation process 1000 may correlate attributes of the e-commerce dataset 220.

Furthermore, instance segmentation process 1000 may be performed with overlapping objects, multiple overlapping objects, different backgrounds, a Region of Interest Align (ROI Align), a class awareness, an instance awareness, anchor boxes, ground truth boxes, object confidence scores and binary masks generated for individual and/or multiple objects. Instance segmentation may be processed by Region proposed networks (RPN), Featured Pyramid Networks (FPN) and Fully Convolutional Networks (FCN). Delineated dental image objects may also be processed in color, gray scale and black and white resolutions.

An example of delineated boundaries of a dental image is shown at the junction between the black background and each gray scale tooth image in instance segmentation dental image 1040. This delineated instance segmentation example depicts five teeth each in a different gray scale. Each delineated bounded image may also be processed and represented in gray scale or color scale. Further, this example may be processed into bounding boxes in different colors. The processed instance segmentation dental images 1040 may be correlated to an e-commerce dataset 220 and provided to an e-commerce provider 132, an e-commerce consumer 133, an e-commerce administrator 135 and/or an e-commerce entity 170.

Figure 11:
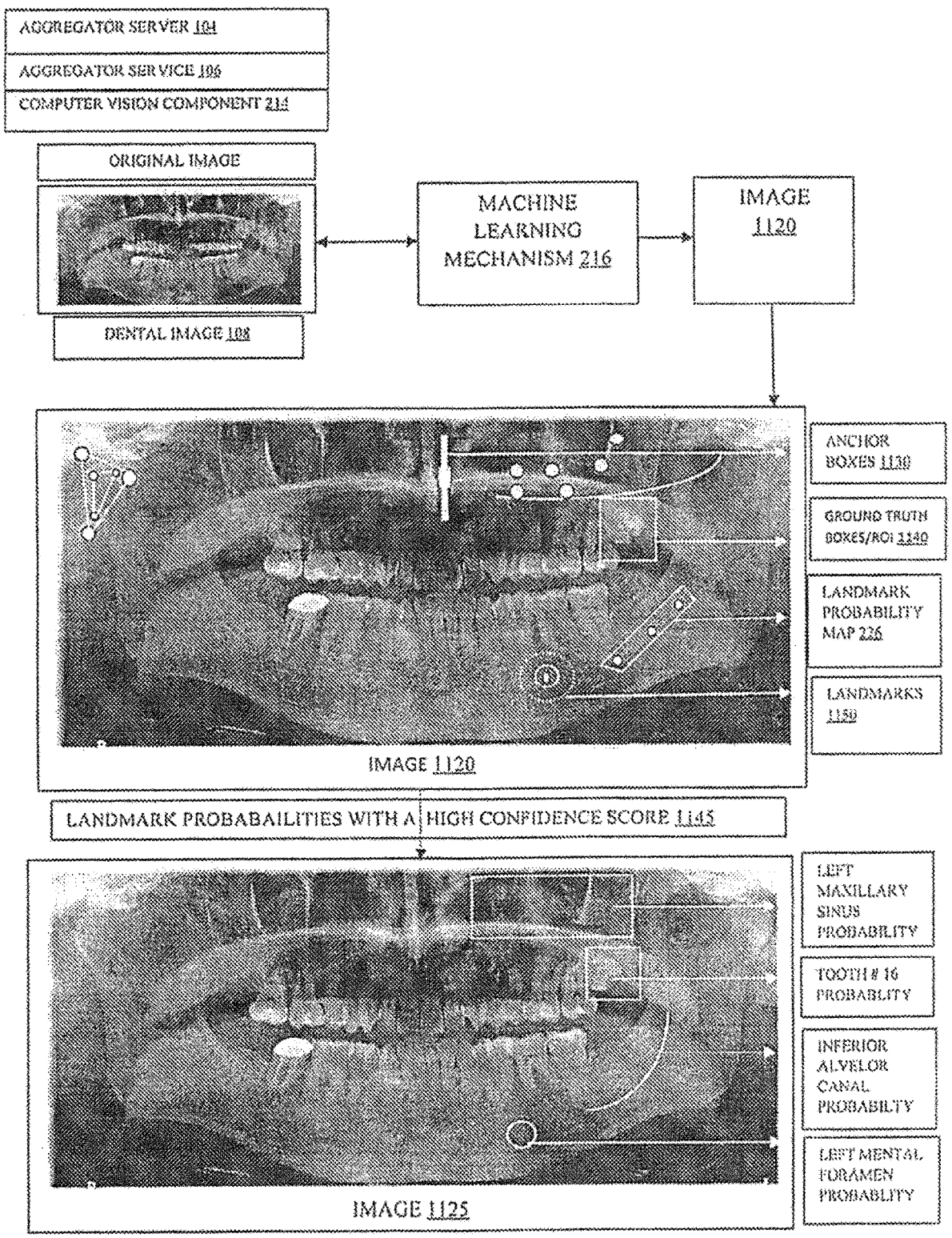
FIG. 11 shows a display diagram of a machine learning mechanism of a dental image being processed with anchor boxes, ground truth boxes, landmarks and landmark probability maps to produce landmark probabilities with high confidence scores, according to an embodiment of the invention.

FIG. 11 shows a display diagram of a machine learning mechanism 216 to produce high confidence landmark probability score 1145 for e-commerce. The aggregator service 106 (executed by the aggregator server 104) may use computer vision component 214 to analyze the dental image 108. In this example, machine learning of dental images may be processed with a function to produce landmark probability maps 226. Wherein a landmark 1150 may be a pixel, a voxel, a loci, a class, a image class, an object class and/or an object. A dental image landmark may be outlined with pixel delineation, a straight line, a curved line, a circle, a square, a rectangle, a triangle and/or a polygon. The dental image 108 may be processed with anchor boxes 1130, ground truth boxes 1140, landmarks 1150, predictive landmarks and landmark probability map 226. Image 1120 shows ground truth boxes 1140, anchor boxes 1130, landmarks 1150 and a landmark probability map 226 placed around high probability anatomical structures. One or more convolutional layers may be configured to extract predictive landmarks from the training of dental images. A convolutional neural network may learn dental image class probabilities maps and dental object class probability maps of the dental image 108. The convolutional neural network may process the dental image 108 with Euclidean geometry and/or extremely randomized forest functions to produce a dental image landmark probability map and spatial relationships of the dental image landmark probability maps. A different dental image landmark probability map is learned for each dental image landmark and the aggregate server may compensate for distorted and/or missing information. The convolutional neural network may then process the dental image class 222 and object class 224 with a machine learning spatial relationship function to determine the spatial relationships between the locations of the dental landmarks and produce a plurality of dental image landmark probability maps. Further the convolutional neural network may machine learn object probability relationships between the locations of the dental images probability maps and machine learn object probability relationships between the locations of the dental image probability maps. An example of a high confidence value for a dental object is shown in image 1125 of a left maxillary sinus. Other examples in dental image 1125 with high confidence scores include a left inferior alveolar nerve canal, $3^{rd}$ molar #16 and the left mental foremen. The aggregate server may provide a probability diagnosis and/or a probability demonstration aid from the plurality of dental image landmark probability maps to an e-commerce provider 132 and/or an e-commerce consumer 133. The processed landmark probability maps may be correlated to an e-commerce dataset 220 and provided to an e-commerce provider 132, an e-commerce consumer 133, an e-commerce administrator 135 and/or a machine learning entity 170.

Figure 12:
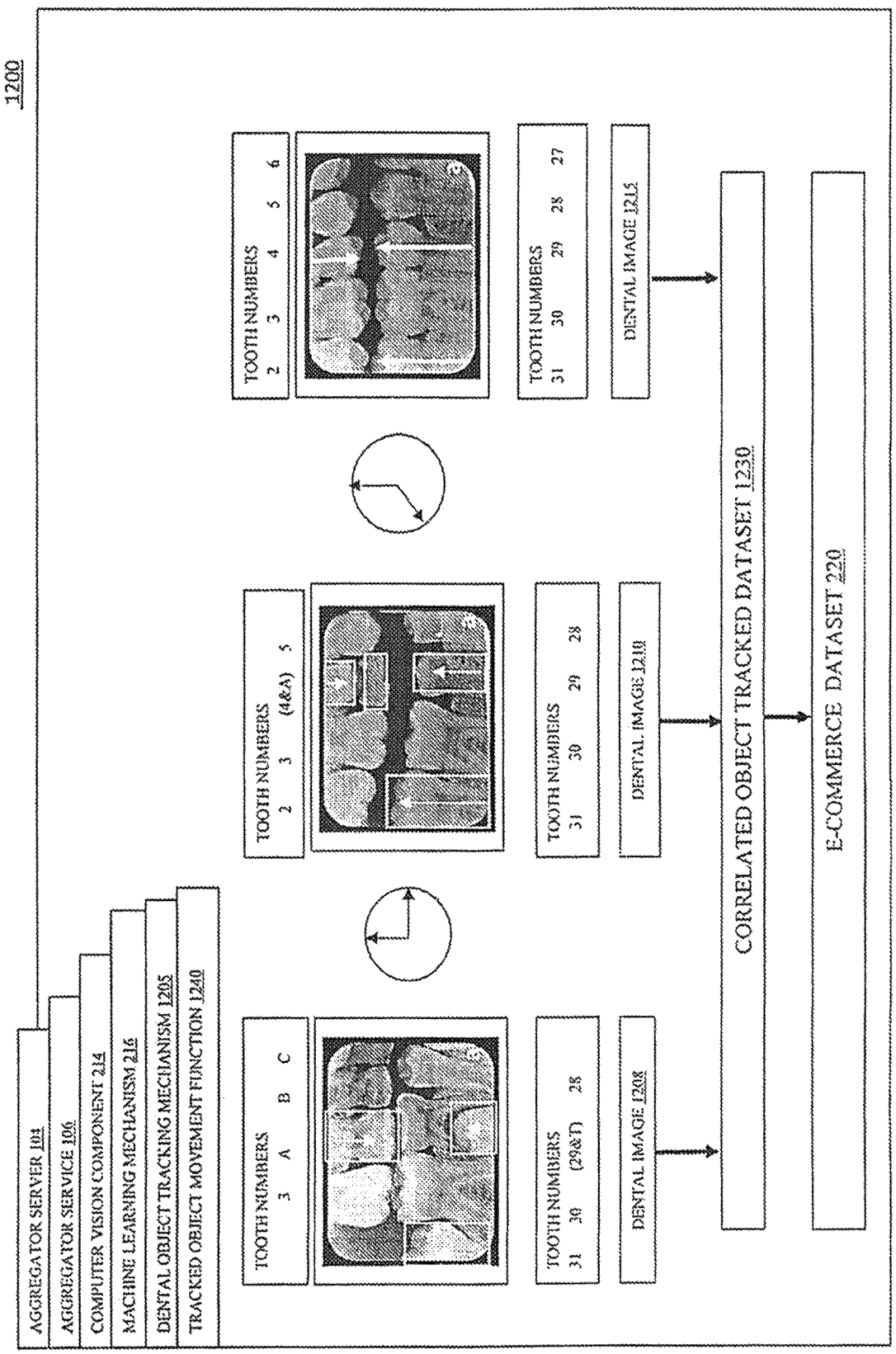
FIG. 12 shows a display diagram of a machine learning mechanism that is object tracking a first dental image then object tracking a second dental image according to the embodiment of the invention.

FIG. 12 shows a display diagram (process 1200) illustrating a dental object tracking mechanism 1205. The aggregator server 104 may use a computer vision component 214 and a machine learning mechanism 216 to execute the aggregator service 106 and process the dental image 1208 for e-commerce with a dental object tracking mechanism 1205. Dental image 1208 of an e-commerce consumer 133 may be processed with a dental object tracking mechanism 1205. Object tracking may use pooling layers, fully connected layers, multiple resolutions, multiple grid components, bounding boxes, a classified image score, an object classification, a semantic segmentation, a instance segmentation, anchor boxes, ground truth boxes, dental image landmark probabilities, image class landmark probabilities, object class landmark probabilities, spatial landmark probability relationships, object probability landmarks, object probability relationships, and dental image landmark probability maps. Further, an object tracked image may be a frame, an image, a layer, a slice and/or a section. A first time interval, dental image 1208 of an e-commerce consumer may be processed and compared with a second time interval dental image 1210 of an e-commerce consumer 133. The second dental image 1210 of an e-commerce consumer 133 may be compared with a third time interval dental image 1215 of an e-commerce consumer. Dental images 1208, 1210 and 1215 may be processed and compared with a tracked object movement function 1240. The tracked object movement function 1240 may further track multiple dental images of an e-commerce consumer 133 over time. The tracked object movement function 1240 may provide the tracked dental image object movements to a correlated object tracked information dataset 1230. Correlated object tracked information dataset 1230 may be provided to an e-commerce dataset 220.

In an example scenario dental image 1208, 1210 and 1215 are dental images of the same e-commerce consumer taken at different time intervals in the same anatomical location. Dental image 1208, 1210 and 1215 may be processed with object classification 840, ROI and ground truth boxes. Dental image 1208 shows a mixed dentition of primary teeth A, B, C and T and adult teeth 3, 28, 29, 30 and 31. Dental image 1210 was taken at a later period in time. Dental image 1210 shows that the primary teeth B and T were exfoliated and primary tooth A is in the process of erupting from the upward eruption force of adult tooth 4. In addition tooth number 2 is not present in dental image 1208 and has erupted into position in dental image 1210. Further, adult tooth number 31 is only partially erupted in dental image 1208. In dental image 1210 number 31 has fully erupted into an adult occlusion. Dental image 1215 was taken in a later period of time after dental image 1210. Dental image 1215 shows no primary teeth and only adult teeth 2,3,4,5,6,27, 28,29,30 and 31. The tracked object movement function 1240 may track, measure and compare the primary and adult teeth movements and provide these object tracking movements to the correlation object tracked information dataset 1230. The correlation object tracked information dataset 1230 may compare the e-commerce consumer object tracked image to a large dataset of dental object tracked movements. The correlation object tracked information dataset 1230 may provide the datasets to an e-commerce dataset 220.

In another example, dental object tracking process 1205 may be performed based on using convolutional neural networks and a machine learning mechanism 216. The dental object tracking process 1205 may be further processed with bounding boxes, an image resizing, multiple resolutions, a ROI, a ROI Align, anchor boxes, Stacked Auto Encoders (SAE), a speech recognition and language processing. Dental image 1208 may be processed with corners, an edge mapping, a roundness, a smoothness, a sharpness and a blurriness and merged into an e-commerce dataset 220.

Dental image objects may be processed at a first resolution and object tracked. The same dental image object may be processed at a second resolution and object tracked. Multiple dental image objects may be processed with multiple resolutions and object tracked. This process may continue and an object tracking dataset may be provided to an e-commerce provider 132, an e-commerce consumer 133, an e-commerce administrator 135 and/or a machine learning entity 170.

Figure 13:
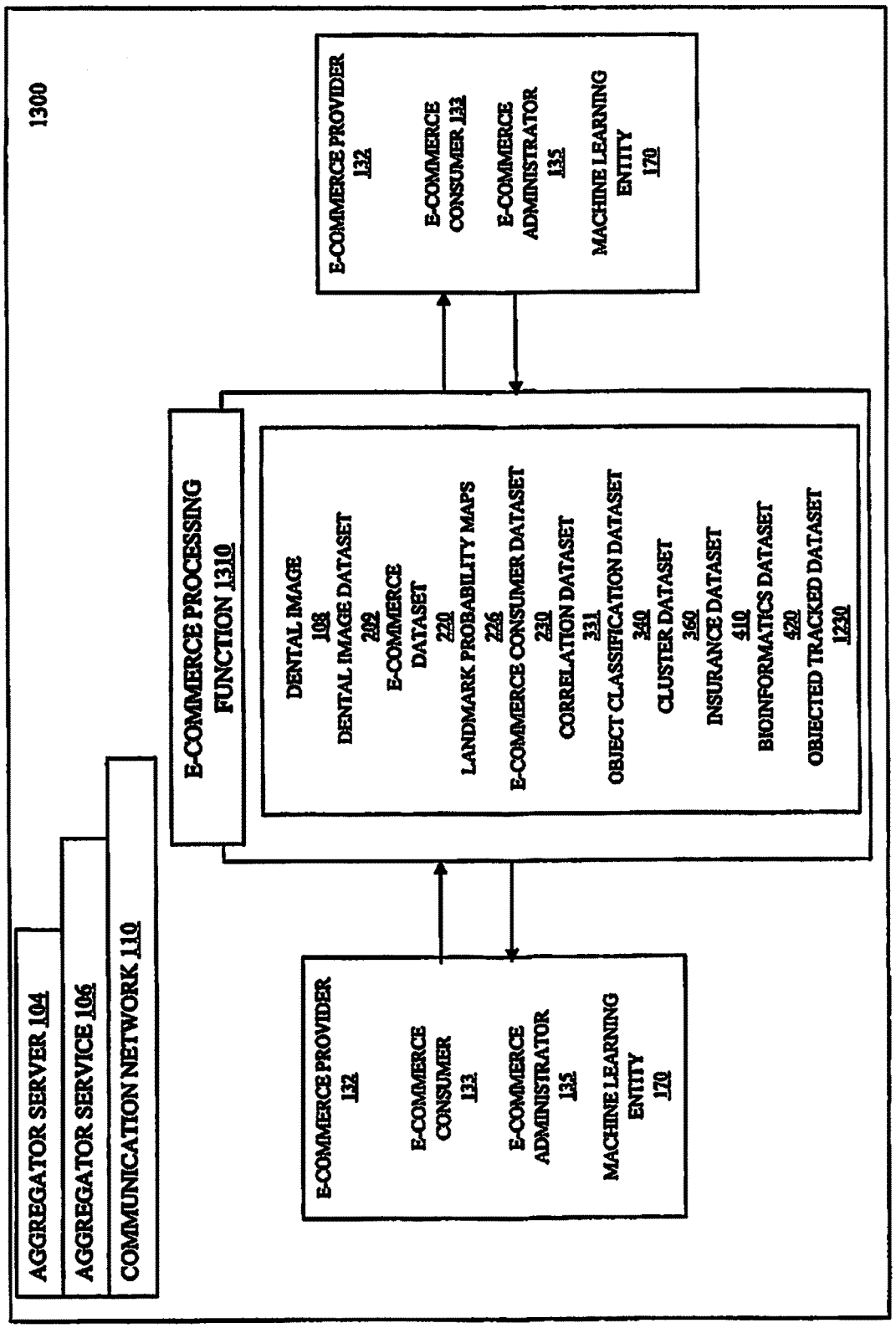
FIG. 13 shows a display diagram of an e-commerce processing function transferring datasets between e-commerce providers, e-commerce consumers, e-commerce administrators and/or a machine learning entity.

FIG. 13 shows a display diagram. The aggregator server 104 may use a communication network 110 to execute the aggregator service 106 and process a transaction of at least one of: an exchange, a transfer, a buy, a sell with at least one of: a dental image 108, an e-commerce consumer dental image, dental image dataset 209, an e-commerce consumer dataset 230, an e-commerce dataset 220 over a communication network, wherein a communication network includes at least one of: the internet, an intranet, an extranet, an internet, an internet transaction service, an online transaction service, a mobile network, a wireless network, an online transaction processing (OLTP) service, an online analytical processing (OLAP) service, a transaction platform, an internet transaction platform. Further, the communication network 110 may exchange, transfer, buy, sell a dental image 108, a dental image dataset 209, an e-commerce dataset 220, a landmark probability map 226, an e-commerce dataset 230, a correlation dataset 331, an object classification dataset 340, a cluster dataset 360, an insurance dataset 410, a bioinformatics dataset 420, and a correlated object tracked dataset 1230 over at least one of: the internet, an intranet, an extranet, an internet, an internet transaction service, an online transaction service, a mobile network, a wireless network, an online transaction processing (OLTP) service, an online analytical processing (OLAP), a transaction platform. Process 1300 may begin with an e-commerce provider 132, an e-commerce consumer 133, an e-commerce administrator 135 and/or a machine learning entity 170 uploading and/or down loading a dental image 108 and/or an e-commerce dataset 220 with an e-commerce processing component 1310. The e-commerce processing function 1310 may upload and/or down load dental images 108 and e-commerce datasets 220 to an e-commerce provider 132, an e-commerce consumer 133, an e-commerce administrator 135 and/or a machine learning entity 170. Further an e-commerce provider 132, an e-commerce consumer 133, an e-commerce administrator 135 and/or a machine learning entity 170 may transfer, exchange, buy and/or sell dental image 108, dental image dataset 209, an e-commerce dataset 220, landmark probability maps 226, an e-commerce dataset 230, a correlation dataset 331, an object classification dataset 340 and a cluster dataset 360, an insurance dataset 410, a bioinformatics dataset 420, and a correlated object tracked dataset 1230 over a communication network, wherein a communication network includes at least one of: the internet, an intranet, an extranet, an internet, an internet transaction service, an online transaction service, a mobile network, a wireless network, an online transaction processing (OLTP) service, an online analytical processing (OLAP) service, a transaction platform.

In an example scenario, the e-commerce processing function 1310, which includes an e-commerce transaction, may exchange, transfer, buy and/or sell at least one of; a dental image 108, a dental image landmark probabilities, a image class landmark probabilities, object class landmark probabilities, a spatial landmark probability relationships, an object probability landmarks, an object probability relationships, a dental image landmark probability maps over a communication network 110. An e-commerce transaction includes at least one of: business to business (B2B), business to consumer (B2C), consumer to business (C2B), consumer to consumer (C2C), business to administration (B2A) and consumer to administration (C2A). The e-commerce processing function 1310 may further received and/or transmit with an e-commerce provider 132, an e-commerce consumer 133, an e-commerce administrator 135, a machine learning entity 170. The e-commerce processing function 1310 may process a transaction of at least one of: a dental image, an e-commerce consumer dental image, dental image dataset, an e-commerce consumer dataset, an e-commerce dataset with at least one of: an e-commerce provider, an e-commerce consumer, an e-commerce administrator, a machine learning entity; wherein a transaction includes at least one of: business to business (B2B), business to consumer (B2C), consumer to business (C2B), consumer to consumer (C2C), business to administration (B2A), consumer to administration (C2A) transactions. At e-commerce processing function 1310, at least one of: a business, consumer, an administrator, a machine learning entity may process a transaction of at least one of: an exchange, a transfer, a buy, a sell of dental images and/or data over a communication network wherein a communication network is at least one of: the internet, an intranet, an extranet, an internet, an internet transaction service, an online transaction service, a mobile network, a wireless network, an online transaction processing (OLTP) service, an online analytical processing (OLAP) service, a transaction platform.

The example scenarios and schemas in FIGS. 1 through 13 are shown with specific components, data types, and configurations. Embodiments are not limited to systems according to these example configurations. Machine learning of dental images for e-commerce may be implemented in configurations employing fewer or additional components in applications and user interfaces. Furthermore, the example schema and components shown in FIGS. 1 through 13 and their subcomponents may be implemented in a similar manner with other values using the principles described herein.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

The invention claimed is:

1. A system for providing machine learning of dental images for e-commerce, the system comprising: an aggregator server, wherein the aggregator server is configured to:
   receive a dental image from at least one of: an e-commerce provider, an e-commerce consumer, an e-commerce administrator, a machine learning entity;
   train the aggregate server to process a first dental image with a deep neural network at a first resolution and provide to a dental image dataset;
   match and identify a plurality of dental image landmark probabilities of a first dental image at a first resolution with a machine learning dental image landmark probabilities dataset and provide to a dental image dataset;
   match and identify image class landmark probabilities of a first dental image at a first resolution with a machine learning image class landmark probabilities dataset and provide to a dental image dataset;
   match and identify object class landmark probabilities of a first dental image at a first resolution with a machine learning object class landmark probabilities dataset and provide to a dental image dataset;
   match and identify spatial landmark probability relationships of a first dental image at a first resolution with a machine learning spatial landmark probability relationships dataset and provide to a dental image dataset;
   match and identify object probability landmarks of a first dental image at a first resolution with a machine learning object probability landmarks dataset and provide to a dental image dataset;
   match and identify object probability relationships of an dental image at a first resolution with a machine learning object probability relationships dataset and provide to a dental image dataset;
   machine learn to generate a dental image landmark probability map of a first dental image at a first resolution and provide to a dental image dataset;

match and identify a dental image landmark probability map of a first dental image at a first resolution with a machine learning dental image landmark probability map dataset and provide to a dental image dataset;

match and identify a plurality of dental image landmark probabilities of a second dental image at a second resolution with a machine learning dental image landmark probabilities dataset and provide to a dental image dataset;

match and identify image class landmark probabilities of a second dental image at a second resolution with a machine learning image class landmark probabilities dataset and provide to a dental image dataset;

match and identify object class landmark probabilities of a second dental image at a second resolution with a machine learning object class landmark probabilities dataset and provide to a dental image dataset;

match and identify spatial landmark probability relationships of a second dental image at a second resolution with a machine learning spatial landmark probability relationships dataset and provide to a dental image dataset;

match and identify object probability landmarks of a second dental image at a second resolution with a machine learning object probability landmarks dataset and provide to a dental image dataset;

match and identify object probability relationships of a second dental image at a second resolution with a machine learning object probability relationships dataset and provide to a dental image dataset;

machine learn to generate a dental image landmark probability map of a second dental image at a second resolution with a machine learning dental image landmark probability map dataset and provide to a dental image dataset;

match and identify a dental image landmark probability map of a second dental image at a second resolution with a machine learning dental image landmark probability map dataset and provide to a dental image dataset;

train the aggregate server to process a first dental image and a second dental image to a large dataset;

merge the first dental image and second dental image into a multiple dental image dataset;

train the aggregate server to process a multiple dental image dataset with a deep neural network with multiple resolutions and provide to a dental image dataset;

match and identify a plurality of dental image landmark probabilities of a multiple dental image dataset at multiple resolutions with a machine learning dental image landmark probabilities dataset and provide to a dental image dataset;

match and identify image class landmark probabilities of a multiple dental image dataset at multiple resolutions with a machine learning image class landmark probabilities dataset and provide to a dental image dataset;

match and identify object class landmark probabilities of a multiple dental image dataset at multiple resolutions with a machine learning object class landmark probabilities dataset and provide to a dental image dataset;

match and identify spatial landmark probability relationships of a multiple dental image dataset at multiple resolutions with a machine learning spatial landmark probability relationships dataset and provide to a dental image dataset;

match and identify object probability landmarks of a multiple dental image dataset at multiple resolutions with a machine learning object probability landmarks dataset and provide to a dental image dataset;

match and identify object probability relationships of a multiple dental image dataset at multiple resolutions with a machine learning object probability relationships dataset and provide to a dental image dataset;

machine learn to generate a dental image landmark probability map of a multiple dental image dataset with multiple resolutions and provide to a dental image dataset;

match and identify a dental image landmark probability map of a multiple dental image dataset at multiple resolutions with a machine learning dental image landmark probability map dataset and provide to a dental image dataset;

correlate a dental image dataset with an e-commerce consumer dataset to produce an e-commerce dataset;

wherein an e-commerce consumer dataset includes least one of: an age, a first name, a gender, a middle initial, a last name, a date of birth, a zip code, an address, a cell phone number, a land line number, a current medication, a previous medication, a social security number, a marital status, an insurance, an insurance identification number, an email address, a change of insurance, a change of employment, a change of zip code, a change of the previous medication, a change of a marital status, a change of gender;

provide an e-commerce dataset to at least one of: an e-commerce provider, an e-commerce consumer, an e-commerce administrator, a machine learning entity;

process transactions between at least one of: an e-commerce provider, an e-commerce consumer, an e-commerce administrator, a machine learning entity;

process a transaction of at least one of: an exchange, a transfer, a buy, a sell with at least one of: a dental image, an e-commerce consumer dental image, a dental image dataset, an e-commerce consumer dataset, an e-commerce dataset over a communication network, wherein a communication network includes at least one of: the internet, an intranet, an extranet, an internet, an internet transaction service, an online transaction service, a cell phone, a mobile network, a wireless network, an online transaction processing (OLTP) service, an online analytical processing (OLAP) service, a transaction platform.

2. The aggregate server of claim 1, wherein the aggregate server is configured to process a transaction of at least one of: a dental image, an e-commerce consumer dental image, a dental image dataset, an e-commerce consumer dataset, an e-commerce dataset with at least one of: an e-commerce provider, an e-commerce consumer, an e-commerce administrator, a machine learning entity; wherein a transaction includes at least one of: business to business (B2B), business to consumer (B2C), consumer to business (C2B), consumer to consumer (C2C), business to administration (B2A), consumer to administration (C2A) transactions.

3. The aggregator server of claim 1, wherein the dental image is obtained from at least one of: a digital x-ray, a digital image, a cell phone, a cell phone captured image, a photographic image, a toothbrush with an imaging device, a toothbrush with an imaging device being a camera, a film based x-ray, a digitally scanned x-ray, a digitally captured x-ray, a scintillator technology based image, a trans-illumination image, a fluorescence technology based image, a blue fluorescence technology based image, a laser based technology based image, a magnetic resonance image (MRI), a computed tomography (CT) scan based image, a cone beam computed tomography (CBCT) image.

4. The aggregator server of claim 1, wherein the e-commerce dental image provider utilizes an image capture device or a data storage device, and wherein the capture image device includes one or more of: an x-ray equipment, a digital camera, a cell phone camera, a scintillator counter, an indirect or direct flat panel detector (FPD), a charged couple device (CCD), a phosphor plate radiography device, a picture archiving and communication system (PACS), a photo-stimulable phosphor (PSP) device, a wireless complementary metal-oxide-semiconductor (CMOS) device.

5. The aggregate server of claim 1, wherein the machine learning of dental images
includes processing the dental image with at least one of:
a sliding window component configured to analyze a dental image;
a multiple grid component to divide and analyze a dental image;
a bounding box component configured to analyze a dental image;
a bounding box component configured to generate an image confidence score for the dental image;
an image classification component configured to generate a dental image confidence score;
an object classification component configured to generate a dental object confidence score;
a semantic segmentation component configured to generate a semantic segmentation of a dental image;
an instance segmentation component configured to generate an instance segmentation of a dental image;
a dental object tracking mechanism configured to track objects in a dental image;
a processor configured to exchange at least one of: a dental image, an e-commerce consumer dental image, a dental image dataset, an e-commerce consumer dataset, an e-commerce dataset with a mobile device;
a processor configured to exchange at least one of: a dental image, an e-commerce consumer dental image, a dental image dataset, an e-commerce consumer dataset, an e-commerce dataset with a cell phone;
a processor configured for an e-commerce consumer to store at least one of: a dental image, an e-commerce consumer dental image, a dental image dataset, an e-commerce consumer dataset, an e-commerce dataset on at least one of: a server, a desktop computer, a workstation, a laptop computer, a cell phone, a tablet, a mobile device, a cloud based storage service;
a processor configured for an e-commerce consumer to process a transaction of at least one of: an exchange, a transfer, a buy, a sell of at least one of: a dental image, a dataset with at least one of: an e-commerce consumer, an e-commerce provider, an e-commerce administrator, a machine learning entity in exchange for at least one of: a currency, a data, a discounts, a product, a goods, a software, an application, an advertisement.

6. The aggregator server of claim 1, wherein the training of the first dental image with a deep neural network occurs concurrently with learning a plurality of dental image landmark probability maps;
training of the second dental image with a deep neural network occurs concurrently with learning a plurality of dental image landmark probability maps;
training of the multiple dental image dataset with a deep neural network occurs concurrently with learning a plurality of dental image landmark probability maps.

7. The aggregator server of claim 1, wherein a different dental image landmark probability map is learned for each dental image landmark and compensates for distorted and missing image information.

8. The aggregator server of claim 1, wherein the e-commerce dental image is processed with:
at least one convolutional neural network layer configured to extract dental image landmark probabilities;
at least one convolutional neural network layer configured to extract image class landmark probabilities;
at least one convolutional neural network layer configured to extract object class landmark probabilities;
at least one convolutional neural network layer configured to extract spatial landmark probability relationships;
at least one convolutional neural network layer configured to extract object probability landmarks;
at least one convolutional neural network layer configured to extract object probability relationships;
at least one convolutional neural network layer configured to extract a dental image landmark probability map.

9. The aggregate server of claim 1, wherein the e-commerce provider includes at least one of: a business, a business entity, a business owner, an employer, a wholesaler, a retailer, a professional, a dentist, a dental hygienist, a physician, a health professional, a veterinarian, a veterinarian professional, a dental professional, a health professional, a group, a research entity, a law enforcement entity, a public administration entity, a government agency, a bioinformatics service, an insurance company, a cloud based storage service;
wherein an e-commerce consumer includes at least one of: an individual, a guardian, a group, an employee;
wherein an e-commerce administrator includes at least one of: an administrator, an administrator entity, a governing agency.

10. The aggregate server of claim 1, wherein the e-commerce dataset is configured to produce:
a diagnostic probability aid for at least one of: an e-commerce consumer, an e-commerce provider, an e-commerce administrator, a machine learning entity;
a probability demonstration aid for at least one of: an e-commerce consumer, an e-commerce provider, an e-commerce administrator, a machine learning entity;
provide at least one of: a diagnostic probability aid, a probability demonstration aid to an e-commerce consumer client device, wherein a client device includes at least one of: a server, a desktop computer, a workstation, a laptop computer, a cell phone, a tablet, a mobile device, a cloud based storage service.

11. The aggregate server of claim 1, wherein the aggregate server is configured to provide at least one of: a probability demonstration aid, a dental object tracking mechanism, a dental image probability diagnosis to at least one of: an e-commerce provider, an e-commerce consumer, an e-commerce administrator, a machine learning entity.

12. An aggregator server for providing machine learning of dental images for e-commerce, the aggregator server comprising:
   a computer vision component configured to analyze the dental image;
   a memory configured to store instructions associated with an aggregator service;
   a processor configured to bidirectional exchange at least one of: a dental image, an e-commerce dental image, a dental image dataset, an e-commerce consumer dataset, an e-commerce dataset with a mobile device;
   a processor configured to bidirectional exchange at least one of: a dental image, an e-commerce consumer dental image, a dental image dataset, an e-commerce consumer dataset, an e-commerce dataset with a cell phone;
      a processor coupled to the computer vision component and the memory, the processor executing the instructions associated with the aggregator service, wherein the aggregator service includes:
      an image processing engine configured to:
      machine learn to generate an image confidence score of a dental image and insert to a dental image dataset;
      machine learn to generate an object confidence score of a dental image and insert to a dental image dataset;
      machine learn to generate a semantic segmentation of a dental image and insert to a dental image dataset;
      machine learn to generate an instance segmentation of a dental image and insert to a dental image dataset;
      machine learn to track an object in a dental image with a dental object tracking mechanism and insert to a dental image dataset;
      receive a dental image from at least one of: an e-commerce provider, an e-commerce consumer, an e-commerce administrator, a machine learning entity;
      train the aggregate server to process a first dental image with a deep neural network at a first resolution and provide to a dental image dataset;
      match and identify a plurality of dental image landmark probabilities of a first dental image at a first resolution with a machine learning dental image landmark probabilities dataset and provide to a dental image dataset;
      match and identify image class landmark probabilities of a first dental image at a first resolution with a machine learning image class landmark probabilities dataset and provide to a dental image dataset;
      match and identify object class landmark probabilities of a first dental image at a first resolution with a machine learning object class landmark probabilities dataset and provide to a dental image dataset;
      match and identify spatial landmark probability relationships of a first dental image at a first resolution with a machine learning spatial landmark probability relationships dataset and provide to a dental image dataset;
      match and identify object probability landmarks of a first dental image at a first resolution with a machine learning object probability landmarks dataset and provide to a dental image dataset;
      match and identify object probability relationships of a dental image at a first resolution with a machine learning object probability relationships dataset and provide to a dental image dataset;
      machine learn to generate a dental image landmark probability map of a first dental image at a first resolution and provide to a dental image dataset;
      match and identify a dental image landmark probability map of a first dental image at a first resolution with a machine learning dental image landmark probability map dataset and provide to a dental image dataset;
      match and identify a plurality of dental image landmark probabilities of a second dental image at a second resolution with a machine learning dental image landmark probabilities dataset and provide to a dental image dataset;
      match and identify image class landmark probabilities of a second dental image at a second resolution with a machine learning image class landmark probabilities dataset and provide to a dental image dataset;
      match and identify object class landmark probabilities of a second dental image at a second resolution with a machine learning object class landmark probabilities dataset and provide to a dental image dataset;
      match and identify spatial landmark probability relationships of a second dental image at a second resolution with a machine learning spatial landmark probability relationships dataset and provide to a dental image dataset;
      match and identify object probability landmarks of a second dental image at a second resolution with a machine learning object probability landmarks dataset and provide to a dental image dataset;
      match and identify object probability relationships of a second dental image at a second resolution with a machine learning object probability relationships dataset and provide to a dental image dataset;
      machine learn to generate a dental image landmark probability map of a second dental image at a second resolution with a machine learning dental image landmark probability map dataset and provide to a dental image dataset;
      match and identify a dental image landmark probability map of a second dental image at a second resolution with a machine learning dental image landmark probability map dataset and provide to a dental image dataset;
         train the aggregate server to process a first dental image and a second dental image to a large dataset;
         merge the first dental image and second dental image into a multiple dental image dataset;
         train the aggregate server to process a multiple dental image dataset with a deep neural network with multiple resolutions and provide to a dental image dataset;
         match and identify a plurality of dental image landmark probabilities of a multiple dental image dataset at multiple resolutions with a machine learning dental image landmark probabilities dataset and provide to a dental image dataset;
         match and identify image class landmark probabilities of a multiple dental image dataset at multiple resolutions with a machine learning image class landmark probabilities dataset and provide to a dental image dataset;

match and identify object class landmark probabilities of a multiple dental image dataset at multiple resolutions with a machine learning object class landmark probabilities dataset and provide to a dental image dataset;

match and identify spatial landmark probability relationships of a multiple dental image dataset at multiple resolutions with a machine learning spatial landmark probability relationships dataset and provide to a dental image dataset;

match and identify object probability landmarks of a multiple dental image dataset at multiple resolutions with a machine learning object probability landmarks dataset and provide to a dental image dataset;

match and identify object probability relationships of a multiple dental image dataset at multiple resolutions with a machine learning object probability relationships dataset and provide to a dental image dataset;

machine learn to generate a dental image landmark probability map of a multiple dental image dataset with multiple resolutions and provide to a dental image dataset;

match and identify a dental image landmark probability map of a multiple dental image dataset at multiple resolutions with a machine learning dental image landmark probability map dataset and provide to a dental image dataset;

correlate a dental image dataset with an e-commerce consumer dataset to produce an e-commerce dataset;

provide an e-commerce dataset to at least one of: an e-commerce provider, an e-commerce consumer, an e-commerce administrator, a machine learning entity;

process transactions between at least one of: an e-commerce provider, an e-commerce consumer, an e-commerce administrator, a machine learning entity;

process a transaction of at least one of: an exchange, a transfer, a buy, a sell with at least one of: a dental image, an e-commerce consumer dental image, a dental image dataset, an e-commerce consumer dataset, an e-commerce dataset over a communication network, wherein a communication network includes at least one of: the internet, an intranet, an extranet, an internet, an internet transaction service, an online transaction service, a mobile network, a cell phone, a wireless network, an online transaction processing (OLTP) service, an online analytical processing (OLAP) service, an internet transaction platform.

13. The aggregate server of claim 12, wherein the e-commerce provider includes at least one of: a business, a business entity, a business owner, an employer, a wholesaler, a retailer, a professional, a dentist, a dental hygienist, a physician, a health professional, a veterinarian, a veterinarian professional, a dental professional, a health professional, a group, a research entity, a law enforcement entity, a public administration entity, a government agency, a bioinformatics service, an insurance company, a cloud based storage service;

wherein an e-commerce consumer includes at least one of: an individual, a guardian, a group, an employee;

wherein an e-commerce administrator includes at least one of: an administrator, an administrator entity, a government agency.

14. The aggregator server of claim 12, wherein the e-commerce consumer dataset is provided to an e-commerce provider upon at least one process to:

verify a compliance of the dental image and the e-commerce consumer dataset with a regulatory policy;

verify an authorization by the e-commerce consumer to analyze the dental image and e-commerce consumer dataset;

authenticate an e-commerce consumer to process a transaction of at least one of: an exchange, a transfer, a buy, a sell of an e-commerce dataset with at least one of: an e-commerce consumer, an e-commerce provider, an e-commerce administrator, a machine learning entity in exchange for at least one of: a currency, a data, a discounts, a product, a goods, a software, an application, an advertisement.

15. The aggregator server of claim 12, wherein the e-commerce consumer dataset includes at least one of an age, a first name, a gender, a middle initial, a last name, a date of birth, a zip code, an address, a cell phone number, a land line number, a current medication, a previous medication, a social security number, a marital status, an insurance, a insurance identification number, a email address, a change of insurance, a change of employment, a change of zip code, a change of the previous medication, a change of the marital status, a change of gender-associated with an e-commerce consumer.

16. The aggregator server of claim 12, wherein the e-commerce provider includes a dental insurance service, and wherein the dental insurance service provides an insurance dataset including at least one of: an American dental association (ADA) code, a date, a claim identifier, a claim number, a duplicate claim associated with the claim identifier, an e-commerce provider national identification number, an e-commerce provider's state license number, a provider identification number may be correlated to an insurance dataset and merged to an e-commerce dataset.

17. The aggregator server of claim 12, wherein the e-commerce provider includes a bioinformatics service, and wherein the bioinformatics service provides a bioinformatics dataset including at least one of: a gene identifier, a gene sequence, a single nucleotide polymorphism, a nucleic acid sequence, a protein sequence, an annotating genome, a shotgun sequence, a periodontal disease, a caries susceptibility, an impacted tooth, a tooth loss, an angle's classification of malocclusion, a diabetes diagnosis to further analyze and integrate the bioinformatics dataset and merge to an e-commerce dataset.

* * * * *